United States Patent
Kammerzell

(10) Patent No.: US 11,713,466 B2
(45) Date of Patent: Aug. 1, 2023

(54) ENGINEERED NUCLEASES IN PLANT GENERATION

(71) Applicant: PIONEER HI-BRED INTERNATIONAL, INC., Johnston, IA (US)

(72) Inventor: Meridith Kammerzell, Fort Collins, CO (US)

(73) Assignee: PIONEER HI-BRED INTERNATIONAL, INC.

(*) Notice: Subject to any disclaimer, the term of this patent is extended or adjusted under 35 U.S.C. 154(b) by 215 days.

(21) Appl. No.: 16/765,570

(22) PCT Filed: Nov. 20, 2018

(86) PCT No.: PCT/US2018/062048
§ 371 (c)(1),
(2) Date: May 20, 2020

(87) PCT Pub. No.: WO2019/104056
PCT Pub. Date: May 31, 2019

(65) Prior Publication Data
US 2020/0308595 A1    Oct. 1, 2020

Related U.S. Application Data

(60) Provisional application No. 62/589,284, filed on Nov. 21, 2017.

(51) Int. Cl.
*C12N 15/82* (2006.01)
*C12N 9/22* (2006.01)

(52) U.S. Cl.
CPC ........... *C12N 15/8213* (2013.01); *C12N 9/22* (2013.01); *C12N 15/8261* (2013.01)

(58) Field of Classification Search
CPC .................................................. C12N 15/82
See application file for complete search history.

(56) References Cited

U.S. PATENT DOCUMENTS

2015/0056705 A1*  2/2015  Conway ............... C12N 15/902
                                                           435/468
2017/0204425 A1*  7/2017  DeKelver .......... C12N 15/8218

FOREIGN PATENT DOCUMENTS

WO    2011049627 A1    4/2011
WO    2017205665 A1    11/2017

OTHER PUBLICATIONS

Munoz, IG, et al., "molecular basis of engineered meganuclease targeting of the endogenous human RAG1 locus", nucleic acids research. Sep. 16, 2010; vol. 39, No. 2: pp. 729-743; abstract; figures 1a, 4; p. 731, col. 2, paragraph 3; p. 739, col. 2, paragraph 2; DOI: 10.1093/nar/gkq801, 2010, 729-743.
Petolino, JF, "genome editing in plants via designed zinc finger nucleases", in vitro cellular and developmental biology. Jan. 29, 2015; pp. 1-8; p. 4, col. 1, paragraph 1; DOI: 10.1007/S11627-015-9663-3, 2015, 1-8.
Donald P. Weeks et al: Use of designer nucleases for targeted gene and genome editing in plants11, Plant Biotechnology Journal, vol. 14, No. 2, Feb. 1, 2016 (Feb. 1, 2016), pp. 483-495, XP055456080, GB.
Manju Gupta et al: Transcri pt i ona l activation of *Brassica napus* ss-ketoacyl-ACP synthase II with an engineered zinc finger protein transcription factor11, Plant Biotechnology Journal, Wiley-Blackwell Publishing Ltd, United Kingdom, vol. 10, No. 7.
Rinaldo Amy R et al: Gene targeting and editing in crop plants: a new era of precision opportunities11, Molecular Breeding: New Strategies in Plant Improvement, Kluwer Academic Publishers, NL, vol. 35, No. 1, Jan. 22, 2015 (Jan. 22, 2015), pp. 1-15, XP035432136.

* cited by examiner

*Primary Examiner* — Brent T Page

(57) ABSTRACT

Methods are provided to mutate, in a targeted manner, the genome of a plant cell using a double stranded DNA break inducing enzyme. Also provided are plants, in particular *Brassica* plants that yield seeds producing oils having a reduced total saturated fatty acid content, and method for making such plants.

10 Claims, 6 Drawing Sheets

Specification includes a Sequence Listing.

FIG. 1 mutant DNA      GGGTGGATGGGGCCAAACTACTCTATTCAAGTGCTTGT------------GCATTCTGAATTCAGCTAACCAC
mutant protein   G  W  M  G  P  N  Y  S  I  S  S  A  C ------------ A  F  * wild-type DNA   GGGTGGATGGGGCCAAACTACTCTATTCAAGTGCTTGTGCTACAAGCAACTTCTGCATTCTGAATTCAGCTAACCAC
wild-type protein G  W  M  G  P  N  Y  S  I  S  S  A  C  A  T  S  N  F  C  I  L  N  S  A  N  H
                                                        meganuclease target

```
mutant DNA       GGGTGGATGGGGCCAAACTACTCTATATCAAGT----------GCTACAAGCAACTTTGCATTCTGAATTCAGCTAAC
mutant protein    G  W  M  G  P  N  Y  S  I  S -----   A   T  S  N  F  C  I  L  N  S  A  N wild-type DNA    GGGTGGATGGGACAAACTACTCTATATCAAGTGCTTGCGCTACAAGCAACTTTGCATTCTGAATTCAGCTAAC
wild-type protein G  W  M  G  T  N  Y  S  I  S  S  A  C  A  T  S  N  F  C  I  L  N  S  A  N
                                                       meganuclease target
```

ENGINEERED NUCLEASES IN PLANT GENERATION

CROSS-REFERENCE TO RELATED APPLICATIONS

This application is a national phase application of PCT/US18/062048, filed 20 Nov. 2018, entitled ENGINEERED NUCLEASES IN PLANT GENERATION, which claims the benefit of U.S. Provisional Patent Application Ser. No. 62/589,284, filed Nov. 21, 2017, and entitled "ENGINEERED NUCLEASES IN PLANT GENERATION", which are hereby incorporated by reference herein in their entirety.

REFERENCE TO A SEQUENCE LISTING SUBMITTED VIA EFS-WEB

The content of the ASCII text file of the sequence listing named "N00568_seqlist_ST25" which is 18.0 kb in size was created on Nov. 19, 2020 and electronically submitted via EFS-Web herewith the application is incorporated by reference in its entirety.

BACKGROUND OF THE INVENTION

In recent years, diets high in saturated fats have been associated with increased levels of cholesterol and increased risk of coronary heart disease. As such, current dietary guidelines indicate that saturated fat intake should be no more than 10 percent of total calories. Based on a 2,000-calorie-a-day diet, this is about 20 grams of saturated fat a day. Oils contain saturated fats. For example canola oil typically contains about 7% to 8% saturated fatty acids. A decrease in saturated fatty acid content would improve the nutritional profile of oils.

SUMMARY OF THE INVENTION

Genes involved in plant oil synthesis, including those that regulate saturated fatty acid and oleic acid content, have been mutated by a process which involves exposing seeds to chemicals or radiation in order to generate mutants with desirable traits. Unlike plants modified with engineered nucleases, in which a mutation (substitution, deletion and/or addition of one or more nucleotides) can be engineered to occur at a very specific location in the plant genome, plants developed via mutagenic processes often result in random, multiple and unspecific genetic changes. These random, multiple genetic changes all come together to provide the phenotype of the mutated plant. With engineered nucleases, a very specific mutation, or set of mutations, can be generated and their effect on phenotype (e.g., oil profile) can be determined.

Provided herein is the production of mutant FatA1, FatA2, Kas2, Kas3 and/or FatB, allele(s) generated by the use of engineered nucleases, plants comprising said one or more mutant alleles of FatA1, FatA2, Kas2, Kas3 and/or FatB, such as *Brassica* plants, and uses of such plants produce lower saturated fatty acid content. As described herein, *Brassica* plants containing such mutations can produce oils with reduced saturated fatty acid content. *Brassica* plants described herein are particularly useful for producing canola oils for certain food applications, as the plants are not genetically modified.

Provided herein are *Brassica* plants (e.g., *Brassica napus, Brassica juncea,* or *Brassica rapa* plants) and progeny thereof (e.g., seeds) that include substitution, deletion and/or insertion mutations in one or more alleles of FatA1, FatA2, Kas2, Kas3 and/or FatB via engineered nucleases, wherein each mutated allele results in the production of a FatA1, FatA2, Kas2, Kas3 and/or FatB polypeptide having reduced or no activity relative to a corresponding wild-type FatA1, FatA2, Kas2, Kas3 and/or FatB polypeptide (alternatively the substitution, deletion and/or insertion may result in no FatA1, FatA2, Kas2, Kas3 and/or FatB protein/activity being produced). A mutated allele can include a nucleic acid encoding a truncated FatA1, FatA2, Kas2, Kas3 and/or FatB polypeptide. A mutated allele can include a sequence having at least 75%, 80%, 85%, 90%, 95%, 96%, 97%, 98%, or 99% sequence identity to the nucleotide sequence of the wild-type allele (e.g., SEQ ID NO: 1 for Kas2).

One aspect provides a method to produce a plant with reduced saturated fatty acids comprising: a) contacting a plant with an engineered nuclease specific for FatA1, FatA2, Kas2, Kas3 and/or FatB gene(s); b) growing the plant from step a) and collecting the seeds from said plant; and c) selecting plants grown from the seeds of step b) with a substitution, deletion and/or insertion mutation in one or more of said genes; wherein said substitution, deletion and/or insertion mutation results in a reduced production of saturated fatty acids by said plant as compared to a control plant of identical genetic background that has not been mutated by said gene editing.

Another aspect provides a method to produce a plant with reduced saturated fatty acids comprising: a) contacting a plant cell or tissue with an engineered nuclease specific for FatA1, FatA2, Kas2, Kas3 and/or FatB gene(s); b) generating a plant from the plant cell or tissue in step a); c) selecting plants of step b) with a substitution, deletion and/or insertion mutation in one or more of said genes; wherein said substitution, deletion and/or insertion mutation results in a reduced production of saturated fatty acids by said plant as compared to a control plant of identical genetic background that has not been mutated by said gene editing.

In one aspect, the plant is a *Cruciferae* plant. In another aspect, the plant is a *Brassica* plant. In another aspect, the plant is *Brassica napus, Brassica juncea,* or *Brassica rapa*. In one aspect, the engineered nuclease is a meganuclease. In one aspect, there is a substitution, deletion and/or insertion mutation in at least one allele of FatA1. In another aspect, there is a substitution, deletion and/or insertion mutation in at least one allele of FatA2. In another aspect, there is a substitution, deletion and/or insertion mutation in at least one allele of Kas2. In one aspect, there is a substitution, deletion and/or insertion mutation in at least one allele of Kas3. In another aspect, there is a substitution, deletion and/or insertion mutation in at least one allele of FatB.

One aspect provides a *Brassica* plant comprising a deletion in at least one allele of FatA1, FatA2, Kas2, Kas3 and/or FatB. In one aspect, the deletion is from about 1 to about 350 base pairs in length. In another aspect, the deletion results in a decrease in saturated fatty acid.

In one aspect, the recognition/target sequence comprises any contiguous nucleotide (e.g., 10 or more) sequence of the Kas2 gene (SEQ ID NO: 1).

In another aspect, provided herein is a method of producing an oil. The method includes crushing seeds produced from at least one plant described herein and extracting the oil from the crushed seeds.

One aspect provides a method to mutate the genome of a *Brassica* plant cell at a target sited comprising: a) inducing a double stranded DNA break at a target site, said double stranded break being induced by the introduction to said cell of a double stranded DNA break inducing (DSBI) enzyme which recognizes a recognition sequence in the vicinity of or at said target site in FatA1, FatA2, Kas2, Kas3 and/or FatB gene(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof. In one aspect, the plant cell is regenerated into a plant. One aspect provides a plant cell comprising a mutation at a target site of the genome obtained by the methods provided herein. Another aspect provides a plant, plant part, seed or propagating material thereof comprising a mutation at a target site of the genome comprising the plant cell.

One aspect provides a method to produce a *Brassica* plant with reduced saturated fatty acids comprising: a) inducing a double stranded DNA break at a target site, said double stranded break being induced by the introduction to a plant cell of a double stranded DNA break inducing (DSBI) enzyme which recognizes a recognition sequence in the vicinity of or at said target site in FatA1, FatA2, Kas2, Kas3 and/or FatB gene(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof; and c) regenerating said plant cell(s) of b) into a plant; wherein said mutation results in reduced production of saturated fatty acids by said plant as compared to a control plant of identical genetic background that has not been mutated by said DSBI and repair.

In one aspect, the DSBI enzyme is a single chain meganuclease or a pair of meganucleases which recognizes or recognize in concert a site and induces or induce said double strand break.

In one aspect, the plant(s) produced by the methods described herein is crossed with another plant.

One aspect provides a plant, plant part, seed or propagating material thereof comprising a modification at a target site of the genome obtained by the methods provided here.

In one aspect, the plant is *Brassica napus, Brassica juncea,* or *Brassica rapa*.

In one aspect, one or both Kas2 alleles on N2 and/or N12 are mutated. In one aspect, one or both Kas2 alleles on N2 are mutated. In another aspect, one or both Kas2 alleles on N12 are mutated. In one aspect, the mutation is a deletion of one or more nucleotides, optionally comprising the substitution of at least one nucleotide.

In one aspect, the plants produced by the methods described herein yield a reduction of stearic acid (18:0) of about 8% to about 17% as compared to a non-mutated plant of identical genetic background. In an another aspect, the plants produced by the methods described herein yield a reduction of palmitic acid (16:0) of about 3% to about 10%, including about 6%, as compared to a non-mutated plant of identical genetic background. In another aspect, the plants yield an overall reduction in total saturated fatty acids of about 1 to about 7%.

BRIEF DESCRIPTION OF THE DRAWINGS

FIG. 1 shows the meganuclease recognition site on the N2 allele used to prepare Kas2-N2 mutant (SEQ ID NO:3) with a 6 bp deletion in the N2 allele. SEQ ID NOs:4-7.

FIG. 2 shows the meganuclease recognition site on the N2 allele used to prepare Kas2-N2 mutant (SEQ ID NO:8) with a 16 bp deletion in the N2 allele. SEQ ID NOs:35, 10, 36, and 12.

FIG. 3 shows the meganuclease recognition site on the N12 allele used to prepare Kas2-N12 mutant (SEQ ID NO:14) with a 51 bp deletion in the N2 allele. SEQ ID NOs:37, 38, 39, and 18.

FIG. 4 shows the meganuclease recognition site on the N12 allele used to prepare Kas2-N2/N12 mutant (SEQ ID NO:19) with a 6 bp deletion in the N12 allele. SEQ ID NOs:20, 21, 40, and 23.

FIG. 5 shows the meganuclease recognition site on the N12 allele used to prepare Kas2-N2/N12 mutant (SEQ ID NO:24) with a 15 bp deletion in the N12 allele. SEQ ID NOs:25-28.

FIG. 6 shows the meganuclease recognition site on the N12 allele used to prepare Kas2-N2/N12 mutant (SEQ ID NO:30) in a IMC201 background with a 13 bp deletion in the N12 allele. SEQ ID NOs:31-34.

DETAILED DESCRIPTION OF THE INVENTION

Methods are provided to mutate, in a targeted manner, the genome of a plant using a double stranded DNA break inducing enzyme. Also provided are plants, in particular *Brassica* plants, which yield seeds producing oils having a reduced saturated fatty acid content, and method for making such plants.

The invention provides methods to introduce a targeted mutation, including insertion, deletion, or substitution of one or more nucleotides, at a precisely localized nucleotide sequence in the genome of a plant using engineered double stranded DNA break inducing enzymes. The invention further provides a plant cell, plant part, plant or seed comprising such a mutated sequence, wherein said mutation results in a reduction of saturated fatty acid production by the plant, and methods for making such plant.

The invention is based on the observation that functional meganucleases can be engineered to specifically recognize and cleave a nucleotide sequence, such as Kas2 (SEQ ID NO: 1), in a plant cell, from which a plant can be produced. Provided herein are plants made by the methods provided herein, such as *Brassica* plants including *B. napus, B. juncea,* and *B. rapa* species of *Brassica*, that yield seeds producing oils having a reduced saturated fatty acid content.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, a "double stranded DNA break endonuclease" is an enzyme capable of inducing a double stranded DNA break at a particular nucleotide sequence, called the "recognition site." Homing endonucleases constitute a family of endonucleases and are sometimes also referred to as meganucleases. They may be encoded by introns, independent genes or intervening sequences, and present structural and functional properties that distinguish them from the more classical restriction enzymes, usually from bacterial restriction-modification Type II systems.

A person skilled in the art would be able to either choose a double stranded DNA break inducing ("DSBI") enzyme recognizing the selected target nucleotide sequence to engineer such a DSBI endonuclease.

As used herein "located in the vicinity" refers to the site of double DNA stranded break induction, i.e. the recognition site of the DSBI enzyme, being located at a distance of 0 bp, 2 bp, 4 bp, 6 bp, 8 bp, 10 bp, 20 bp, 30 bp, 50 bp, 60 bp, 70 bp, 80 bp, 90 bp, 100 bp, 200, 250 bp, 500 bp, 1 kbp, 2 kbp, 3 kbp, 4 kbp, 5 kbp to 10 kbp from the target, i.e. the site in the genomic DNA which is to be mutated (the target site).

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism).

The expression "operably linked" means that said elements of the chimeric gene are linked to one another in such a way that their function is coordinated and allows expression of the coding sequence, i.e. they are functionally linked. By way of example, a promoter is functionally linked to another nucleotide sequence when it is capable of ensuring transcription and ultimately expression of said other nucleotide sequence.

A nullizygous organism carries two mutant or missing alleles for the same gene. The mutant/missing alleles are both complete loss-of-function or 'null' alleles, so homozygous null and nullizygous are synonymous.

A gene knockout (abbreviation: KO) is a genetic technique in which both of an organism's alleles are made inoperative ("knocked out" of the organism). The term knockout, inactivated, and disrupted are used interchangeably herein to mean that the targeted site is changed so that the gene expression product is eliminated or greatly reduced or the product expressed has reduced activity as compared to a control (e.g., wild type protein). Also known as knockout organisms or simply knockouts. The term also refers to the process of creating such an organism, as in "knocking out" a gene.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The optimal alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Nucleic acids can be DNA or RNA, single- or double-stranded. Nucleic acids can be synthesized chemically or produced by biological expression in vitro or in vivo. Nucleic acids can be chemically synthesized using appropriately protected ribonucleoside phosphoramidites and a conventional DNA/RNA synthesizer. DNA includes cDNA and genomic DNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

The terms "comprises," "comprising," and the like can have the meaning ascribed to them in U.S. Patent Law and can mean "includes," "including" and the like. As used herein, "including" or "includes" or the like means including, without limitation.

Brassica Plants

Brassica plants described herein have reduced levels of total saturated fatty acids in the seed oil as a result of reduced activity of FatA1, FatA2, Kas2, Kas3 and/or FatB. It is understood that throughout the disclosure, reference to "plant" or "plants" includes progeny, i.e., descendants of a particular plant or plant line, as well as cells or tissues from the plant. Progeny of an instant plant include seeds formed on $F_1$, $F_2$, $F_3$, $F_4$ and subsequent generation plants, or seeds formed on $BC_i$, $BC_2$, $BC_3$, and subsequent generation plants. Seeds produced by a plant can be grown and then selfed (or outcrossed and selfed, or doubled through dihaploid) to obtain seeds homozygous for a mutant allele. The term "allele" or "alleles" refers to one or more alternative forms of a gene at a particular locus.

Reduced activity, including absence of detectable activity, of FatA1, FatA2, Kas2, Kas3 and/or FatB, can be achieved by mutating one or more endogenous FatA1, FatA2, Kas2, Kas3 and/or FatB allele(s) (each of these genes has one or more isoforms, for example, Kas2 has six isoforms, including one on each of chromosome N2 and N12, as well as two on N7 and two on N16; however, modification of isoforms on N7 and N16 has not demonstrated a reduction in saturates). An endogenous isoform/allele of FatA1, FatA2, Kas2, Kas3 and/or FatB allele can be mutated (deletion, addition and/or substitution mutation) by the use of engineered nucleases.

Genetic mutations can be introduced within, for example, regenerable plant tissue using one or more engineered nucleases. The treated population, or a subsequent generation of that population, can be screened for reduced protein activity that results from the mutation, e.g., by determining the fatty acid profile of the population and comparing it to a corresponding non-mutagenized population. Mutations can be in any portion of a gene, including coding sequence, intron sequence and regulatory elements, that render the resulting gene product non-functional or with reduced activity.

The plants on which the genetic mutations can be carried out are any plants, including those in the *Brassica* family, including any wild-type and mutant plant backgrounds. Such *Brassica* plants include, but are not limited to, IMC201 (U.S. Pat. No. 9,334,483), IMC02 (represented by American Type Culture Collection (ATCC) Accession No. PTA-6221), Westar (U.S. Pat. No. 6,342,658), 1904 (represented by American Type Culture Collection (ATCC) Accession No. PTA-11273, as well as progeny of the seed designated 1904 and represented by ATCC Accession No. PTA-11273), 2558 (represented by American Type Culture Collection (ATCC) Accession No. PTA-11274, as well as progeny of the seed designated 2558 and represented by ATCC Accession No. PTA-11274), US Pub Appln No. 2013/0081156, 95CB504 (U.S. Pat. No. 9,334,483), Cargill background (represented by American Type Culture Collection (ATCC) Accession No. PTA-12314, PTA-12315 and PTA-12316), 03LC LL and hybrid backgrounds deposited as Accession No. PTA-12314, PTA-12315 and PTA-12316, and Topas (represented by American Type Culture Collection (ATCC) Accession No. PTA-120738).

Engineered Nucleases

The use of engineered nucleases (GEEN) is a type of genetic engineering in which DNA is inserted, deleted or substituted in the genome of an organism using engineered nucleases, or "molecular scissors." These nucleases create site-specific double-strand breaks (DSBs) at desired locations in the genome. The induced double-strand breaks are repaired resulting in targeted mutations, such as deletions.

There are currently four families of engineered nucleases being used: meganucleases, zinc finger nucleases (ZFNs), Transcription Activator-Like Effector-based Nucleases (TALEN), and the CRISPR-Cas system (Esvelt, K M. and Wang, H H. (2013). "Genome-scale engineering for systems and synthetic biology." Mol Syst Biol 9 (1): 641; Tan, W S. et al. (2012). "Precision editing of large animal genomes." Adv Genet 80: 37-97; Puchta, H. and Fauser, F. (2013). "Gene targeting in plants: 25 years later." Int. J. Dev. Biol 57: 629-637; Boglioli, E. and Richard, M. "Rewriting the book of life: a new era in precision genome editing" (PDF). Boston Consulting Group; Method of the Year 2011. Nat Meth 9 (1), 1-1; www.sciencemag.org/topic/2015-breakthrough-year).

Meganucleases, found commonly in microbial species, have the unique property of having long recognition sequences (>14 bp) thus making them naturally specific (de Souza, N., Primer: genome editing with engineered nucleases. Nat Meth 9 (1), 27-27 (2011); Smith, J. et al., A combinatorial approach to create artificial homing endonucleases cleaving chosen sequences. Nucleic Acids Research 34 (22), e149 (2006)). This can be exploited to make site-specific DSB in genome editing. Meganuclease variants that recognize unique sequences have been created (Id). Also of use is the fusion of various meganucleases to create hybrid enzymes that recognize a new sequence (Chevalier, B. S. et al., Design, Activity, and Structure of a Highly Specific Artificial Endonuclease" Molecular Cell 10 (4), 895-905 (2002)). Yet others have altered the DNA interacting amino acids of the meganuclease to design sequence specific meganucelases in a method named rationally designed meganuclease (U.S. Pat. No. 8,021,867; WO2007/047859; WO2011/064736).

A well characterized megaendonuclease is I-SceI. I-SceI is a site-specific endonuclease, responsible for intron mobility in mitochondria in *Saccharomyces* cerevisea. The enzyme is encoded by the optional intron Sc LSU.1 of the 21 S rRNA gene and initiates a double stranded DNA break at the intron insertion site generating a 4 bp staggered cut with 3'OH overhangs. The recognition site of I-SceI endonuclease extends over an 18 bp non-symmetrical sequence (Colleaux et al. 1988 Proc. Natl. Acad. Sci. USA 85: 6022-6026). The amino acid sequence for I-SceI and a universal code equivalent of the mitochondrial I-SceI gene have been provided by e.g. WO 96/14408. WO 96/14408 further discloses a number of variants of I-SceI protein which are still functional. PCT application PCT/EP04/013122 (incorporated herein by reference) provides synthetic nucleotide sequence variants of I-SceI which have been optimized for expression in plants.

Another well characterized designed meganuclease is based on the naturally occurring meganuclease I-CreI for use as a scaffold. I-CreI is an endonuclease found in the chloroplasts of *Chlamydomonas rheinhardti* (Thompson et al. 1992, Gene 119, 247-251). This endonuclease is a homodimer that recognizes a pseudo-palindromic 22 bp DNA site in the 23SrRNA gene and creates a double stranded DNA break that can be used for the introduction of an intron. I-CreI is a member of a group of endonucleases carrying a single LAGLIDADG (SEQ ID NO: 22) motif. LAGLIDADG (SEQ ID NO: 29) enzymes contain one or two copies of the consensus motif. Single-motif enzymes, such as I-CreI function as homodimers, whereas double-motif enzymes are monomers with two separate domains. Accordingly, when designing meganucleases derived from an I-CreI scaffold to recognize a 22 bp nucleotide sequence of interest, two monomeric units are designed, each recognizing a part of the 22 bp recognition site, which are needed in concert to induce a double stranded break at the 22 bp recognition site (WO2007/047859). Concerted action may be achieved by linking the two monomeric units into one single chain meganuclease, or may also be achieved by promoting the formation of heterodimers, as described e.g. in WO2007/047859.

A list of other DSB inducing enzymes and their respective recognition sites is provided in Table I of WO 03/004659 (pages 17 to 20) (incorporated herein by reference). These include I-See I, I-Chu I, I-Dmo I, I-Cre I, I-Csm I, PI-Fli I, Pt-Mtu I, I-Ceu I, I-See II, I-See III, HO, PI-Civ I, PI-Ctr I, PI-Aae I, PI-BSU I, PI-Dhal, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fae I, PI-Mja I, PI-Pho I, PI-Tag I, PI-Thy I, PI-Tko I or PI-Tsp I.

As opposed to meganucleases, the concept behind ZFNs and TALEN technology is based on a non-specific DNA cutting enzyme, which can then be linked to specific DNA sequence recognizing peptides, such as zinc fingers (such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530)) and transcription activator-like effectors (TALEs; Baker, M., Gene-editing nucleases. Nat Meth 9 (1), 23-26 (2012); Christian et al., 2010, Genetics 186: 757-761, WO10/079430 and WO10/146121). In these technologies, the endonuclease has a DNA recognition site and cleaving site separate from each other. Although the nuclease portions of both ZFNs and TALEN constructs have similar properties (e.g., FokI), the difference between these engineered nucleases is in their DNA recognition peptide. ZFNs rely on Cys2-His2 zinc fingers and TALEN constructs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities (de Souza, N., Primer: genome editing with engineered nucleases. Nat Meth 9 (1), 27-27 (2011)). Zinc fingers have been more established in these terms and approaches such as modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries among other methods have been used to make site specific nucleases.

Another way of producing custom-made meganucleases, by selection from a library of variants, is described in WO2004/067736. Custom made meganucleases with altered sequence specificity and DNA-binding affinity may also be obtained through rational design as described in WO2007/047859. Such custom designed endonucleases are also referred to as a non-naturally occurring endonucleases.

The designed double stranded break inducing enzyme may comprise, but need not comprise, a nuclear localization signal (NLS), such as the NLS of SV40 large T-antigen (Raikhel, Plant Physiol. 100: 1627-1632 (1992) and references therein) (Kalderon et al. Cell 39: 499-509 (1984)). The nuclear localization signal may be located anywhere in the protein, but is conveniently located at the N-terminal end of the protein. The nuclear localization signal may replace one or more of the amino acids of the double stranded break inducing enzyme.

Conveniently, the DSBI enzyme can be provided by expression of a plant expressible recombinant gene(s) encoding such enzyme(s). To this end, a DNA region comprising a nucleotide sequence encoding, for example, a designed meganuclease or meganuclease monomeric unit can be operably linked to a plant-expressible promoter and optionally a DNA region involved in transcription termination and polyadenylation and introduced into a plant, plant part or plant cell(s). The recombinant gene(s) encoding DSBI enzyme may be introduced transiently or stably. The DSBI enzyme may also be introduced into the plant, plant part or plant cell(s) by introducing into the cell an RNA molecule which is translated into the DSBI enzyme. Alternatively, the DSBI enzyme may be introduced into the plant, plant part or plant cell(s) directly as a protein. Methods for the introduction of DNA or RNA molecules or proteins into a plant, plant part, tissue or plant cell(s) are available to an art worker and briefly described below.

Described herein, the term "plant operative promoter" and "plant-expressible promoter" mean a promoter which is capable of driving transcription in a plant, plant tissue, plant organ, plant part, or plant cell. This includes any promoter of plant origin, but also any promoter of non-plant origin which is capable of directing transcription in a plant cell.

Promoters that may be used in this respect are constitutive promoters, such as the promoter of the cauliflower mosaic virus (CaMV) 35S transcript (Hapster et al., 1988, Md. Gen. Genet. 212: 182-190), the CaMV 19S promoter (U.S. Pat. No. 5,352,605; WO 84/02913; Benfey et al., 1989, EMBO J. 8:2195-2202), the subterranean clover virus promoter No 4 or No 7 (WO 96/06932), the Rubisco small subunit promoter (U.S. Pat. No. 4,962,028), the ubiquitin promoter (Holtorf et al., 1995, Plant Mal. Biol. 29:637-649), T-DNA gene promoters such as the octopine synthase (OCS) and nopaline synthase (NOS) promoters from *Agrobacterium*, and further promoters of genes whose constitutive expression in plants is available to the person skilled in the art.

Further promoters that may be used in this respect are tissue-specific or organ-specific promoters, such as seed-specific promoters, such as the 2S albumin promoter (Joseffson et al., 1987, J. Biol. Chem. 262:12196-12201), the phaseolin promoter (U.S. Pat. No. 5,504,200; Bustos et al., 1989, Plant Cell 1. (9):839-53), the legumine promoter (Shirsat et al., 1989, Mal. Gen. Genet. 215(2):326-331), the "unknown seed protein" (USP) promoter (Baumlein et al., 1991, Mal. Gen. Genet. 225(3):459-67), the napin promoter (U.S. Pat. No. 5,608,152; Stalberg et al., 1996, Planta 199: 515-519), the *Arabidopsis* oleosin promoter (WO 98/45461), the *Brassica* Bce4 promoter (WO 91/13980), and further promoters of genes whose seed-specific expression in plants is available to the person skilled in the art.

Plant Gene Editing

The use of meganucleases, ZFNs, CRISPR and TALEN, provides a novel strategy for genetic manipulation in plants and can assist in the engineering of desired plant traits by mutating endogenous genes.

Using engineered nucleases, or any method available to an art worker, various genes can be mutated (so as to create a deletion mutation/truncation, addition of one more nucleotides and/or mutating one or more nucleotides (changing its sequence/substitution) and not a mutation by insertion of foreign/non-endogenous DNA), including FatA1 (fatty acyl thioesterase A 1; Moreno-Perez et al. 2012. Reduced expression of FatA thioesterases in *Arabidopsis* affects the oil content and fatty acid composition of the seeds. Planta 235: 629-39; Hawkins & Kridl. 1998. Characterization of acyl-ACP thioesterases of mangosteen (Garcinia mangostana) seed and high levels of stearate production in transgenic canola. Plant J 13: 743-52); FatA2 (fatty acyl thioesterase A 2; U.S. Pat. No. 9,334,483); Kas3 (Dehesh et al. 2001. Overexpression of 3-ketoacyl-acyl-carrier protein synthase IIIs in plants reduces the rate of lipid synthesis. Plant Phys 125:1103-1114; Abbadi et al. 2000. Knockout of the regulatory site of 3-ketoacyl-ACP synthase III enhances short- and medium-chain acyl-ACP synthesis. Plant J 24: 1-9); Kas2 (Pidkowich et al. 2007. Modulating seed β-ketoacyl-acyl carrier protein synthase II level converts the composition of a temperate seed oil to that of a palm-like tropical oil.

PNAS 104:4742-4747; Wu et al. 1994. A mutant of *Arabidopsis* deficient in the elongation of palmitic acid. Plant Phys 106: 143-150; Gupta et al. 2012. Transcriptional activation of *Brassica napus* β-ketoacyl-ACP synthase II with an engineered zinc finger protein transcription factor. Plant Biotech J 10:783-791); and/or FATB (acyl-acyl carrier protein thioesterases; Bonaventure, G. (2003) Plant Cell. April 15 (4) 1020-33; PCT/EP2008/005551; PCT/US2010/061226) of a plant, such as a Cruciferae plant, for example a *Brassica* plant, including a plant of the *Brassica napus, Brassica juncea,* or *Brassica rapa* species. In one aspect, the plant is an oilseed crop, such as flax (*Linum* sp.), rapeseed (*Brassica* sp.), soybean (Glycine sp.), sunflower (*Helianthus* sp.), cotton (*Gossypium* sp.), corn (*Zea mays*), olive (*Olea* sp.), safflower (Carthamus sp.), cocoa (*Theobroma* cacoa), peanut (*Arachis* sp.), hemp, oil palm, coconuts, groundnuts, sesame seed, castor bean, *lesquerella*, tallow tree, shea nuts, poppy seed, and/or jojoba seeds. Thus, provided herein are genes and plants, such as *Brassica* plants, that include modified alleles of, for example FatA1, FatA2, Kas2, Kas3 and/or FatB, that result in the production of the protein encoded by the gene to have reduced activity or no activity (as compared to wild type FatA1, FatA2, Kas2, Kas2 and/or FatB) or results in little to no protein product being produced.

For example, through use of a targeted/designed meganuclease and endogenous repair mechanisms, an insertion, substitution or deletion mutation can be created in any one of the genes described herein. A deletion mutation can be from 1 nucleotide to 400 plus nucleotides in length, including for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 342, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400 and so on (and any range encompassing such numbers or the entire gene). Such deletions can result in little to no expression of the gene (RNA and/or protein) and if protein is expressed from the gene, it will have no or reduced activity as compared to a wild type gene.

The engineered nuclease is provided to plants or plant tissues via conventional methods (e.g., DNA coding for engineered nuclease is inserted into a plasmid (generally operably linked components comprising a promoter sequence, engineered nuclease, terminator (stop) sequence and optionally an antibiotic resistance gene)) which is then introduced into the plant cells by any method available to the art, including for example into bacteria, such as *Agrobacterium tumefaciens*, but also by direct DNA transfer methods. Various methods for DNA delivery into cells/tissues (intact plant cells or partially degraded tissues or plant cells) are known in the art, and include electroporation as illustrated in U.S. Pat. No. 5,384,253; microprojectile bombardment (biolistics) as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; protoplast transformation as illustrated in U.S. Pat. No. 5,508,184, electroporation, chemically-assisted transformation, liposome-mediated transformation (see, e.g., A. Deshayes, et al. (1985) EMBO J. 4:2731-7.), carbon fiber, silicon carbide fiber or aluminum borate fiber (generally termed whiskers) (see, e.g., J. Brisibe, Exp. Bot. 51 (343): 187-196 (2000); Dunwell (1999) Methods Mol. Biol. 111:375-82; and U.S. Pat. No. 5,464,765), microinjection (see, e.g., T J. Reich, of al. (1986) Biotechnology 4: 1001-1004) and viral-mediated transformation (see, e.g., S. B. Gelvin, (2005) Nat Biotechnol. 23: 684-5, WO 90/12107, WO 03/052108 and WO 2005/098004), bombardment of plant cells with heterologous foreign DNA adhered to particles, ballistic particle acceleration, aerosol beam transformation (U.S. Patent Application No. 20010026941; U.S. Pat. No. 4,945,050; International Publication No. WO 91/00915; U.S. Patent Application No. 2002015066, WO 01/038514; all incorporated herein by reference), Led transformation, PEG transformation, and various other non-particle direct-mediated methods to transfer DNA. As used herein "direct DNA transfer" is any method of DNA introduction into plant cells which does not involve the use of natural *Agrobacterium* spp. and which is capable of introducing DNA into plant cells.

It will also be clear that the terms used to describe the method such as "introduction of a DNA" as well as "regeneration of a plant from the cell" do not imply that such DNA necessarily needs to be introduced by transformation techniques. Indeed, it will be immediately clear to the person skilled in the art that the DNA molecule of interest may also be introduced by breeding or crossing techniques from one plant to another. Thus, "introducing" in connection with the present application relate to the placing of genetic information in a plant cell or plant by any known means. This can be effected by any method known in the art for transforming RNA or DNA into plant cells, tissues, protoplasts or whole plants or by introgressing said RNA or DNA into plants as described below.

In the case of introducing DNA into a plant, plant tissue or pant cell(s) in which the mutation is desired (e.g., canola plant or plant tissue; including, for example, several varieties of the Brassicaceae plants, including for example, *Brassica napus, Brassica rapa, B. campestris* or *Brassica juncea* and mutated *Brassica* plants) via *Agrobacterium tumefaciens*, the plant, plant tissues, or plant cell(s) is exposed to the bacteria carrying the engineered nuclease. For example, the plant can be dipped in a solution comprising the bacterium or disks can be punched out from a plant leaf (or other plant tissue, such as the stems, can be used) and incubated with a culture of plasmid-containing *A. tumefaciens*. The disks/plant tissue are then placed under conditions to generate callus in the presence of antibiotic. Only those plant cells/tissue that have DNA from the plasmid (the resistance gene) will have antibiotic resistance. The conditions therefore select for the plant cells/tissue by killing those that do not contain plasmid DNA. After resistant callus is selected, they are transferred to medium that induces growth of shoots, where they grow roots, and then to soil to grow into mature plants.

Plants (offspring) are then selected for those which have a mutation in the desired gene (e.g., such as those listed above). The selection process can look for altered size in the gene of interest and/or protein activity (protein normally produced by the gene of interest), as well as antibiotic resistance (an extra piece of DNA that was included in the plasmid inserted into the bacteria that provides for resistance to a specific antibiotic) or by sequence. Those plants with reduced to no activity in the desired gene (expression of RNA and/or protein), as compared to plants that were not exposed to the engineered nuclease (with identical starting backgrounds), are of particular interest. If the bacteria inserted any foreign DNA into the plant, these plants can be further bred until such DNA is no longer part of the mutated plant. The plants can also be bred so that they are homozygous for the mutation (e.g., deletion).

Also provided is a method crossing one or more first parent plants that contain a mutant allele at one or more loci of FatA1, FatA2, FatB, Kas2, and/or Kas3 and one or more second parent plants that contain a mutant allele at a different locus of FatA1, FatA2, FatB, Kas2, and/or Kas3, wherein each mutant allele results in the production of a polypeptide having reduced activity (or no activity) relative to a corresponding wild-type (or a gene that was not mutated as described herein) FatA1, FatA2, FatB, Kas2, and/or Kas3 polypeptide (or no polypeptide is produced at all); and selecting progeny plants having mutants alleles at two or more different loci thereby obtaining a desired plant.

Plant Products

Oils obtained from such plants, such as *Brassica* plants (canola oil), can have low or no saturated fatty acids and an altered stearic or palmitic acid fatty acid content as compared to a plant that was not mutated as described herein (identical genetic background to plant prior to exposure to an engineered nuclease). Oil content in the seeds can be determined by methods known to those of skill in the art.

In another aspect, a method of producing an oil is provided. The method includes crushing seeds produced from at least one *Brassica* plant described herein; and extracting oil from the crushed seeds. Such oils can be used in food compositions, spray coatings for food, and/or for frying applications (such as frying food, so as to produce fried foods such as snack chips (e.g., corn or potato chips), French fries, or other quick serve foods).

The invention will be further described in the following examples, which do not limit the scope of the invention described in the claims.

EXAMPLES

Example 1

Mutation of Kas2 with Use of a Meganuclease

Using a meganuclease specific for Kas2 (SEQ ID NO:1) (the expression of the desired meganuclease in a canola plant cell causes specific breaks in Kas2 DNA in the plant genome; repair of which leads to deletions, insertions and/or base pair changes), several canola plants with deletions in Kas2 were generated (ranging from 1 to 350 base pair deletions). This resulted in phenotypes with a decrease in C18:0 saturated fat production from about 8% to about 17%, a reduction in 16:0 of about 0% to about 10% (including about 6%) and with a reduction in combined C18:0/C20:0/C22:0/C24:0 from about 12% to about 19%, as compared to plants with an identical genetic background to the plant prior to exposure to an engineered nuclease.

Thus targeted mutation of Kas2 resulted in a significant and unexpected decrease in saturated fat production.

Figure 1:
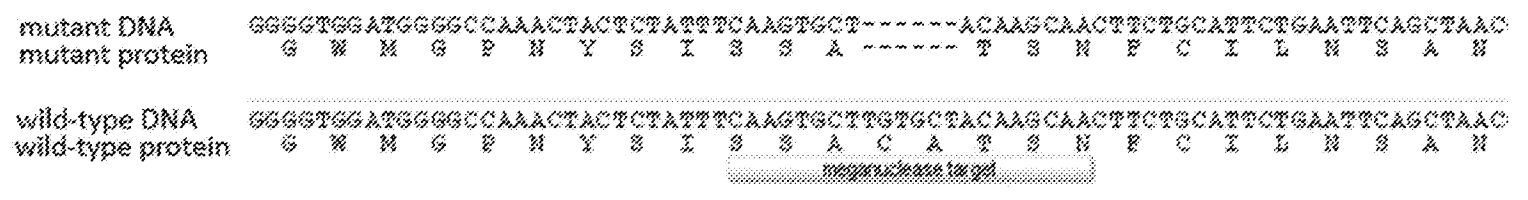

A meganuclease specific for Kas2 was used to prepare a mutant in the N2 allele. SEQ ID NO:2 is the region of the wild type N2 allele that was selected for mutation. A Kas2-N2 mutant (SEQ ID NO:3) with a 6 bp deletion in the N2 allele was generated. FIG. 1 shows the meganuclease recognition site on the N2 allele. SEQ ID NO:4 is the sequence of the meganuclease recognition site on the N2 allele of the Kas2-N2 mutant. SEQ ID NO:5 is the amino acid translation of the meganuclease recognition site on the N2 allele of the Kas2-N2 mutant. SEQ ID NO: 6 is the sequence of the meganuclease recognition site on the N2 allele of the wild type Kas2. SEQ ID NO:7 is the amino acid translation of the meganuclease recognition site on the N2 allele of the wild type Kas2.

A meganuclease specific for Kas2 was used to prepare a mutant in the N2 allele. SEQ ID NO:2 is the region of the wild type N2 allele that was selected for mutation. A Kas2-N2 mutant (SEQ ID NO:8) with a 16 bp deletion in the N2 allele was generated. FIG. 2 shows the meganuclease recognition site on the N2 allele. SEQ ID NO:9 is the sequence of the meganuclease recognition site on the N2 allele of the Kas2-N2 mutant. SEQ ID NO:10 is the amino acid translation of the meganuclease recognition site on the N2 allele of the Kas2-N2 mutant. SEQ ID NO: 11 is the sequence of the meganuclease recognition site on the N2 allele of the wild type Kas2. SEQ ID NO:12 is the amino acid translation of the meganuclease recognition site on the N2 allele of the wild type Kas2.

Figure 3:
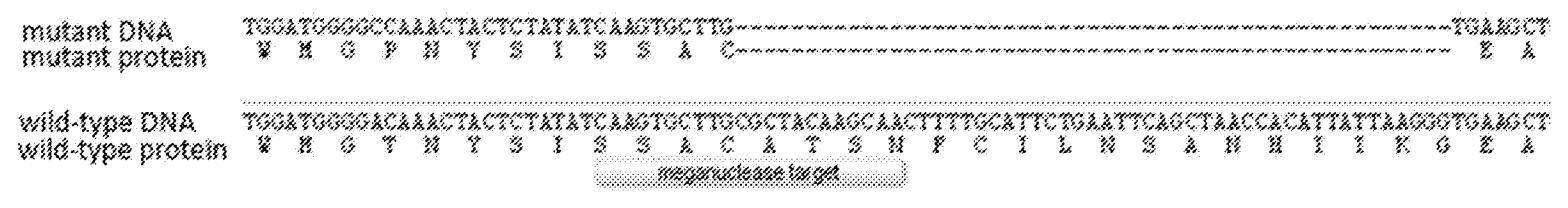

A meganuclease specific for Kas2 was used to prepare a mutant in the N12 allele. SEQ ID NO:13 is the region of the wild type N12 allele that was selected for mutation. A Kas2-N12 mutant (SEQ ID NO:14) with a 51 bp deletion in the N12 allele was generated. FIG. 3 shows the meganuclease recognition site on the N12 allele. SEQ ID NO:15 is the sequence of the meganuclease recognition site on the N12 allele of the Kas2-N12 mutant. SEQ ID NO:16 is the amino acid translation of the meganuclease recognition site on the N12 allele of the Kas2-N12 mutant. SEQ ID NO: 17 is the sequence of the meganuclease recognition site on the N12 allele of the wild type Kas2. SEQ ID NO:18 is the amino acid translation of the meganuclease recognition site on the N12 allele of the wild type Kas2.

A meganuclease specific for Kas2 was used to prepare a mutant in the N12 allele of a Kas2-N2 mutant. A Kas2-N2/N12 double mutant (SEQ ID NO:19) with a deletion in the N2 allele and a 6 bp deletion in the N12 allele was generated. FIG. 4 shows the meganuclease recognition site on the N12 allele. SEQ ID NO:20 is the sequence of the meganuclease recognition site on the N12 allele of the Kas2-N2/N12 mutant. SEQ ID NO:21 is the amino acid translation of the meganuclease recognition site on the N12 allele of the Kas2-N2/N12 mutant. SEQ ID NO: 22 is the sequence of the meganuclease recognition site on the N12 allele of the wild type Kas2. SEQ ID NO:23 is the amino acid translation of the meganuclease recognition site on the N12 allele of the wild type Kas2.

Figure 5:
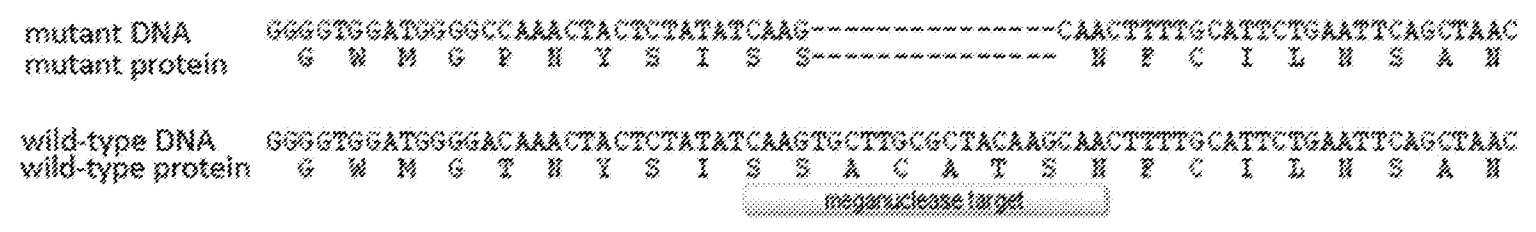

A meganuclease specific for Kas2 was used to prepare a mutant in the N12 allele of a Kas2-N2 mutant. A Kas2-N2/N12 double mutant (SEQ ID NO:24) with a deletion in the N2 allele and a 15 bp deletion in the N12 allele was generated. FIG. 5 shows the meganuclease recognition site on the N12 allele. SEQ ID NO:25 is the sequence of the meganuclease recognition site on the N12 allele of the Kas2-N2/N12 mutant. SEQ ID NO:26 is the amino acid translation of the meganuclease recognition site on the N12 allele of the Kas2-N2/N12 mutant. SEQ ID NO: 27 is the sequence of the meganuclease recognition site on the N12 allele of the wild type Kas2. SEQ ID NO:28 is the amino acid translation of the meganuclease recognition site on the N12 allele of the wild type Kas2.

Figure 6:
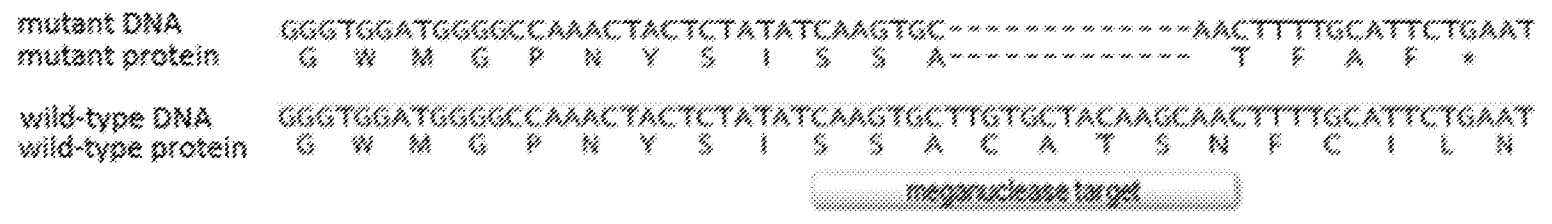

A meganuclease specific for Kas2 was used to prepare a mutant in the N12 allele of a Kas2-N2 mutant in a IMC201 background. SEQ ID NO:29 is the region of the wild type N12 allele that was selected for mutation. A Kas2-N2/N12 double mutant (SEQ ID NO:30) with a deletion in the N2 allele and a 13 bp deletion in the N12 allele was generated. FIG. 6 shows the meganuclease recognition site on the N12 allele. SEQ ID NO:31 is the sequence of the meganuclease recognition site on the N12 allele of the Kas2-N2/N12 mutant. SEQ ID NO:32 is the amino acid translation of the meganuclease recognition site on the N12 allele of the Kas2-N2/N12 mutant. SEQ ID NO: 33 is the sequence of the meganuclease recognition site on the N12 allele of the wild type Kas2. SEQ ID NO:34 is the amino acid translation of the meganuclease recognition site on the N12 allele of the wild type Kas2.

Example 2

Kas2 Mutation and Analysis

The Kas2 mutants described above were grown and tested for saturated fatty acid production.

In the Tables provided below, the fatty acids are referred to by the length of the carbon chain and number of double bonds within the chain. For example, C14:0 refers to myristic acid; C16:0 refers to palmitic acid; C18:0 refers to stearic acid; C18:1 refers to oleic acid; C18:2 refers to linoleic acid; C18:3 refers to ALA; C20:0 refers to archidic acid; C20:1 refers to eicosenoic acid; C22:0 refers to behenic acid; C22:1 refers to erucic acid; C24:0 refers to lignoceric acid; and C24:1 refers to nervonic acid. "Total Sats" refers to the total of C14:0, C16:0, C18:0, C20:0, C22:0, and C24:0. Representative fatty acid profiles are provided for each of the specified samples.

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 1-3) and saturated fatty acid production (Tables 1, 2, 3, 4, and 5).

The average results of saturated fatty acid production in said mutant plant lines is presented in Table 1 (Cargill background), Table 2 (Cargill background) and Table 3 (Cargill background), Table 4 (Cargill background), Table 5 (IMC201 background), showing mutated plant lines, prepared by the methods described herein having a reduction of saturated fatty acid 18:0 (stearic acid) of about 8% to about 17%, a reduction in 18/20/22/24 saturated fatty acids combined of about 8% to about 19%, a reduction in 16:0 of about 0% to about 10% (including about 6%), and a reduction in total saturated fatty acids of about 1% to about 7%. "WT" indicates average results for non-mutated (e.g., wild-type allele(s)) plants of the identical genetic background.

TABLE 1

| Sample | C18:0 | % reduction C18:0 | C20:0 | C22:0 | C24:0 | Total Sats 18/20/22 | % reduction 18/20/22/24 | Total Sats | % reduction total sats |
|---|---|---|---|---|---|---|---|---|---|
| Kas2-N2 Mutant | 1.25 | 14% | 0.35 | 0.15 | 0.11 | 1.85 | 16% | 5.12 | 4% |
| Wild-Type | 1.45 | | 0.41 | 0.18 | 0.15 | 2.19 | | 5.36 | |

TABLE 2

| Sample | C18:0 | % reduction C18:0 | C20:0 | C22:0 | C24:0 | Total Sats 18/20/22 | % reduction 18/20/22/24 | Total Sats | % reduction total sats |
|---|---|---|---|---|---|---|---|---|---|
| Kas2-N12 Mutant | 1.31 | 10% | 0.36 | 0.15 | 0.11 | 1.93 | 12% | 5.31 | 1% |
| Wild-Type | 1.45 | | 0.41 | 0.18 | 0.15 | 2.19 | | 5.36 | |

TABLE 3

| Sample | C16:0 | % reduction C16:0 | C18:0 | % reduction C18:0 | C20:0 | C22:0 | C24:0 | Total Sats 18/20/22/24 | % reduction 18/20/22/24 | Total Sats | % reduction total sats |
|---|---|---|---|---|---|---|---|---|---|---|---|
| Kas2-N2/N12 Mutant | 2.99 | 6% | 1.33 | 8% | 0.33 | 0.13 | 0.1 | 1.89 | 14% | 4.96 | 7% |
| Wild-Type | 3.17 | | 1.45 | | 0.41 | 0.18 | 0.15 | 2.19 | | 5.36 | |

TABLE 4

| Sample | C18:0 | % reduction C18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| Kas2-N2/N12(x) Mutant (6 bp deletion in N12) | 1.30 | 17% | 0.33 | 0.12 | 0.12 | 1.87 | 19% | 4.72 | 7% |
| Kas2-N2/N12(y) Mutant (15 bp deletion in N12) | 1.37 | 13% | 0.34 | 0.12 | 0.14 | 1.96 | 15% | 4.90 | 4% |
| Wild-Type | 1.57 | | 0.43 | 0.17 | 0.15 | 2.32 | | 5.10 | |

TABLE 5

| Sample | C18:0 | % reduction C18:0 | C20:0 | C22:0 | C24:0 | Total Sats 18/20/ | % reduction 18/20/22 | Total Sats | % reduction total sats |
|---|---|---|---|---|---|---|---|---|---|
| Kas2-N12 Mutant | 2.25 | 9% | 0.67 | 0.29 | 0.15 | 3.36 | 8% | 7.76 | 5% |
| Wild-Type IMC201 | 2.46 | | 0.71 | 0.31 | 0.17 | 3.65 | | 8.16 | |

BIBLIOGRAPHY

D'Halluin et al. 2013. Targeted molecular trait stacking in cotton through targeted double-strand break induction. Plant Biotech J 11:933-41.

Djukanovic et al. 2013. Male-sterile maize plants produced by targeted mutagenesis of the cytochrome P450-like gene (MS26) using a re-designed I-CreI homing endonuclease. The Plant Journal 76:888-99.

Gao et al. 2010. Heritable targeted mutagenesis in maize using a designed endonuclease. The Plant Journal 61:176-187.

Honig et al. 2015. Transient expression of virally delivered meganuclease in planta generates inherited genomic deletions. Mol Plant 8:1292-4.

Puchta & Fauser. 2014. Synthetic nucleases for genome engineering in plants: prospects for a bright future. The Plant Journal 78:727-741.

Sprink et al. 2015. Plant genome editing by novel tools: TALEN and other sequence specific nucleases. Current Opinion in Biotech 32:47-53.

Tzfira et al. 2012. Genome modifications in plant cells by custom-made restriction enzymes. Plant Biotech Journal 10:373-389.

All patents, patent applications, accession numbers and publications cited herein are incorporated herein by reference in their entirety.

SEQUENCES

```
SEQ ID NO: 1 (Brassica napus) Kas2, wild type
atggtggctg  cctcttcctg  ttacgcctat  ttggacttta  ggccttgcaa  tcactacaac    60
aacaacaaca  acgccttgtc  ttctctcttc  ggatcaaata  gtatttcttt  gaatcaaaac   120
cagagtagat  tgaaccgagc  aactaactcc  ggtagagcat  tcttcttttg  ccgcgtcttc   180
ctgttaaagt  ttttttttt   taatgtttgc  tcacacaagt  ctttgtttca  tgttgttatg   240
gtttttatgt  tattgggcaa  atgatgaaac  ttgtaggtaa  tttttattgt  gagtttcaga   300
ctagatataa  ggactatgtg  gatacatagt  ttggagacct  gcataaatgg  cagtcaaact   360
atatatataa  actatgaagt  tgcatggaac  ttaattgata  taatgccatt  gagatgaggt   420
ttatgaatag  tagctaatta  attttaagta  actccatcgt  caacttataa  tgtgttatgt   480
tgtttttagg  tagagccatg  gctattgcta  tgaatatgga  aaatgaagcc  atggttagca   540
agaataatcc  ccctatggag  aagcgtcggg  ttgtggtgac  aggcatggga  gttgaaacat   600
cattaggtca  tgacccacat  accttttacg  agaacttgct  acaaggaaac  agtggtatta   660
gccacattga  ggattttgat  tgttctgact  ttcctacggt  aaataagcaa  atattattat   720
catattatat  caagactttc  ttggtatctt  tgtgggttc   tttatttact  atctttcctt   780
tgtttttaaa  ttttgttcaa  gagaatcgcg  ggtgagatca  aatctttctc  cactgaagga   840
tgggttgctc  ctaaactgtc  taggaggatg  gacaagttca  tgctctatct  cctcactgct   900
ggcaagaaag  ctttggctga  tggtggtgta  accgaacaag  tcatggctga  gtttgacaaa   960
gccaaatgtg  gcgtttttgat tggctctgca  ctgggtggca  tgaaggtctt  tcatgaggct  1020
attcaagctt  tgaagatctc  ttacaagaag  atgaatcctc  tttgtgttcc  tcttgctaca  1080
actaacatgg  gttctgctat  gcttgctgtt  gatctggtgt  ctgattaaat  ctgaatgtta  1140
atataaacaa  aatatgaatg  aacaacactg  acgtttcttt  tcaaatgata  aataggggtg  1200
gatggggcca  aactactcta  tttcaagtgc  ttgtgctaca  agcaacttct  gcattctgaa  1260
ttcagctaac  cacattatta  agggtgaagc  tgtaagtatc  ctacatccac  ttggaaactc  1320
aaaagtttgg  tagaactact  ttattagact  gtctcctaaa  cctttcagga  tgtaatgcta  1380
tgtggtggct  cagatgcagc  tattattcca  ataggtcaa   actctctctc  tctcctgcac  1440
tgctctttga  agtttaagat  acatgtatct  tattgtatgt  gtaccagtgc  agggttggca  1500
ggtttcgtgg  cagtccgggc  tctttcacaa  aggaataatg  atcccgcaaa  agcttcacgt  1560
ccttgggatt  gtgtaatttt  cttacactgc  atcgaagttc  tgtcaatagg  accttccctt  1620
acatgtctgt  aatgttgaag  gaagtttaat  gtgttgaaat  gtgtgtatta  tgttttttgta 1680
acagaatcga  gatggtttcg  tgattgggga  gggagctgga  gttctgcttt  tggaagaact  1740
tgagcatgct  aaggtatata  acttattaca  aatgaaactt  atctcgttct  tgccatggaa  1800
```

| SEQUENCES | | | | | |
|---|---|---|---|---|---|
| aaagttgtaa | gaacttatgt | attttgattt | tatgttttca | gaaaagagga | gcaactatct | 1860
| acgcagagtt | tcttggtggg | agcttcacat | gtgatgccta | ccacatgacc | gagcctcacc | 1920
| ctgatggtag | tttcattttc | ccctatttca | tattagtttg | ccattaaccc | atgtctaaat | 1980
| atccacagga | gctggtgtga | ttatatgtat | tgagagagcg | ttagctcatg | ctgggattcc | 2040
| caaggaacag | ataaaattacg | tcaatgcaca | tgcaacctca | acaccagctg | gagaccttaa | 2100
| ggagtacaaa | gccctggttc | actgttttgg | tcaaaatcct | gaggtagttt | catttttca | 2160
| gtcctcaagt | ttagtatctt | agaaaatgtt | acaagattcc | aaggtagttt | tatgtgcttt | 2220
| tcttatttgc | tcctctcact | atgttggcag | ctaaaggtaa | actccacgaa | atcgatgatc | 2280
| ggacacttgc | tgggagctgc | tggtgctgta | gaggctgttg | caaccgtgca | ggtaagacaa | 2340
| taaatattag | agactggtgt | cagttttctc | agttttcatg | ctaattttct | tttggtttct | 2400
| aaaggcaata | agaaccggtt | gggttcatcc | aaatatcaac | ctagacaatc | cagagaatgg | 2460
| agtggtatgt | tgttgttttt | tgccttattg | ttattcaaag | atgatcatat | tttgatacta | 2520
| gtattctaca | caaagaccat | ttaatgtcca | taataaaagt | tttaataata | ctacctaatg | 2580
| ttatgaaact | ggagcaggat | acaaaattgc | tggtgggttc | taagaaggag | agattgaaca | 2640
| ttaaagcagc | cttgtcaaat | tcttttgggt | ttggtggtca | taactccagc | atcattttg | 2700
| ctccttacaa | gtga | | | | | 2714

SEQ ID NO: 2 (Brassica napus) Kas 2, wild type
| tgatggtggt | gtaaccgaac | aagtcatggc | tgagtttgac | aaagccaaat | gtggcgtttt | 60
| gattggctct | gcactgggtg | gcatgaaggt | ctttcatgag | gctattcaag | ctttgaagat | 120
| ctcttacaag | aagatgaatc | ctttttgtgt | tcctcttgct | acaactaaca | tgggttctgc | 180
| tatgcttgct | gttgatctgg | tgtctgatta | aatctgaatg | ttaatataaa | caaaatatga | 240
| atgaacaaca | ctgacgtttc | ttttcaaatg | ataaataggg | gtggatgggg | ccaaactact | 300
| ctatttcaag | tgcttgtgct | acaagcaact | tctgcattct | gaattcagct | aaccacatta | 360
| ttaagggtga | agctgtaagt | atcctacatc | cacttggaaa | ctcaaaagtt | tggtagaact | 420
| actttattag | actgtctcct | aaacctttca | ggatg | | | 455

SEQ ID NO: 3 Artificial Sequence (from Brassica napus) Kas2, N2 mutant (6 bp deletion in N2), in a Cargill background
| tgatggtggt | gtaaccgaac | aagtcatggc | tgagtttgac | aaagccaaat | gtggcgtttt | 60
| gattggctct | gcactgggtg | gcatgaaggt | ctttcatgag | gctattcaag | ctttgaagat | 120
| ctcttacaag | aagatgaatc | ctttttgtgt | tcctcttgct | acaactaaca | tgggttctgc | 180
| tatgcttgct | gttgatctgg | tgtctgatta | aatctgaatg | ttaatataaa | caaaatatga | 240
| atgaacaaca | ctgacgtttc | ttttcaaatg | ataaataggg | gtggatgggg | ccaaactact | 300
| ctatttcaag | tgctacaagc | aacttctgca | ttctgaattc | agctaaccac | attattaagg | 360
| gtgaagctgt | aagtatccta | catccacttg | gaaactcaaa | agtttggtag | aactactta | 420
| ttagactgtc | tcctaaacct | ttcaggatg | | | | 449

SEQ ID NO: 4 Artificial Sequence (from Brassica napus) meganuclease recognition site of Kas2 N2 mutant (6 bp deletion in N2)
| ggggtggatg | gggccaaact | actctatttc | aagtgctaca | agcaacttct | gcattctgaa | 60
| ttcagctaac | | | | | | 70

SEQ ID NO: 5 Artificial Sequence (from Brassica napus) amino acid translation of meganuclease recognition site of Kas2 N2 mutant (6 bp deletion in N2)
Gly Trp Met Gly Pro Asn Tyr Ser Ile Ser Ser Ala Thr Ser Asn Phe
1               5                   10                  15
Cys Ile Leu Asn Ser Ala Asn
            20

SEQ ID NO: 6 (Brassica napus) meganuclease recognition site of wild type Kas2
| ggggtggatg | gggccaaact | actctatttc | aagtgcttgt | gctacaagca | acttctgcat | 60
| tctgaattca | gctaac | | | | | 76

SEQ ID NO: 7 (Brassica napus) amino acid translation of meganuclease recognition site of wild type Kas2
Gly Trp Met Gly Pro Asn Tyr Ser Ile Ser Ser Ala Cys Ala Thr Ser
1               5                   10                  15
Asn Phe Cys Ile Leu Asn Ser Ala Asn
            20                  25

SEQ ID NO: 8 Artificial Sequence (from Brassica napus) Kas2 N2 mutant in a Cargill background (16 bp deletion in N2)
| tgatggtggt | gtaaccgaac | aagtcatggc | tgagtttgac | aaagccaaat | gtggcgtttt | 60
| gattggctct | gcactgggtg | gcatgaaggt | ctttcatgag | gctattcaag | ctttgaagat | 120
| ctcttacaag | aagatgaatc | ctttttgtgt | tcctcttgct | acaactaaca | tgggttctgc | 180
| tatgcttgct | gttgatctgg | tgtctgatta | aatctgaatg | ttaatataaa | caaaatatga | 240
| atgaacaaca | ctgacgtttc | ttttcaaatg | ataaataggg | gtggatgggg | ccaaactact | 300
| ctatttcaag | tgcttgtgca | ttctgaattc | agctaaccac | attattaagg | gtgaagctgt | 360
| aagtatccta | catccacttg | gaaactcaaa | agtttggtag | aactacttta | ttagactgtc | 420
| tcctaaacct | ttcaggatg | | | | | 439

SEQ ID NO: 9 Artificial Sequence (from Brassica napus) meganuclease recognition site of Kas2 mutant

| SEQUENCES |
| --- |

```
gggtggatg  gggccaaact  actctatttc  aagtgcttgt  gcattctgaa  ttcagctaac    60
cac                                                                     63
```

SEQ ID NO: 10 Artificial Sequence (from *Brassica napus*) amino acid
translation of meganuclease recognition site of Kas2 mutant
Gly Trp Met Gly Pro Asn Tyr Ser Ile Ser Ser Ala Cys Ala Phe
1               5                   10                  15

SEQ ID NO: 11 (*Brassica napus*) meganuclease recognition site of wild type
Kas2
```
ggggtggatg  gggccaaact  actctatttc  aagtgcttgt  gctacaagca  acttctgcat    60
tctgaattca  gctaaccac                                                    79
```

SEQ ID NO: 12 (*Brassica napus*) amino acid translation of meganuclease
recognition site of wild type Kas2
Gly Trp Met Gly Pro Asn Tyr Ser Ile Ser Ser Ala Cys Ala Thr Ser
1               5                   10                  15
Asn Phe Cys Ile Leu Asn Ser Ala Asn His
            20                  25

SEQ ID NO: 13 (*Brassica napus*) wild type partial sequence of Kas2 (N12)
```
cgggtgagat  caaatctttc  tcaactgaag  gatgggttgc  tcctaaactg  tctaggagga    60
tggacaagtt  catgctctat  cttctcactg  ctggcaagaa  agctttggct  gatggtggtg   120
taaccgaaca  agtcatggct  gagtttgaca  aagccaaatg  tggcattttg  attggctctg   180
cactgggtgg  catgaaggtc  tttcatgagg  ctattcaagc  tttgaagatc  tcttacaaga   240
agatgaatcc  tttttgtgtt  cctcttgcta  caactaacat  gggttctgct  atgctcgcta   300
ttgatctggt  ctggtctggt  ctaaatgtga  atgttatata  aacaaaatat  gaatgaacaa   360
ccactgacgt  ttcttttcaa  atgataaatt  aggggtggat  ggggccaaac  tactctatat   420
caagtgcttg  cgctacaagc  aacttttgca  ttctgaattc  agctaaccac  attattaagg   480
gtgaagctgt  aagtatctcc  taaactctgt  ttggtagact  tctcttctgg  ttttacttta   540
ttagactgtc  ttgtctttcc  cctaaacctt  tca                                 573
```

SEQ ID NO: 14 Artificial Sequence (from *Brassica napus*) partial sequence
of Kas2 N12 mutant
```
cgggtgagat  caaatctttc  tcaactgaag  gatgggttgc  tcctaaactg  tctaggagga    60
tggacaagtt  catgctctat  cttctcactg  ctggcaagaa  agctttggct  gatggtggtg   120
taaccgaaca  agtcatggct  gagtttgaca  aagccaaatg  tggcattttg  attggctctg   180
cactgggtgg  catgaaggtc  tttcatgagg  ctattcaagc  tttgaagatc  tcttacaaga   240
agatgaatcc  tttttgtgtt  cctcttgcta  caactaacat  gggttctgct  atgctcgcta   300
ttgatctggt  ctggtctggt  ctaaatgtga  atgttatata  aacaaaatat  gaatgaacaa   360
ccactgacgt  ttcttttcaa  atgataaatt  aggggtggat  ggggccaaac  tactctatat   420
caagtgcttg  tgaagctgta  agtatctcct  aaactctgtt  tggtagactt  ctcttctggt   480
tttactttat  tagactgtct  tgtctttccc  ctaaacctt   ca                      522
```

SEQ ID NO: 15 Artificial Sequence (from *Brassica napus*) meganuclease
recognition site of Kas2 mutant
```
tggatggggt  ggatgggggcc  aaactactct  atttcaagtg  cttgtgaagc  t            51
```

SEQ ID NO: 16 Artificial Sequence (from *Brassica napus*) amino acid
translation of meganuclease recognition site of Kas2 mutant
Trp Met Gly Thr Asn Tyr Ser Ile Ser Ser Ala Cys Glu Ala
1               5                   10

SEQ ID NO: 17 (*Brassica napus*) meganuclease recognition site of wild type
Kas2
```
tggatggggt  ggatgggggcc  aaactactct  atttcaagtg  cttgtgctac  aagcaacttc   60
tgcattctga  attcagctaa  ccacattatt  aagggtgaag  ct                      102
```

SEQ ID NO: 18 (*Brassica napus*) amino acid translation of meganuclease
recognition site of wild type Kas2
Trp Met Gly Thr Asn Tyr Ser Ile Ser Ser Ala Cys Ala Thr Ser Asn
1               5                   10                  15
Phe Cys Ile Leu Asn Ser Ala Asn His Ile Ile Lys Gly Glu Ala
            20                  25                  30

SEQ ID NO: 19 Artificial Sequence (from *Brassica napus*) partial sequence
for a Kas2 N12 mutant in a Cargill background (6 bp deletion in N12)
```
cgggtgagat  caaatctttc  tcaactgaag  gatgggttgc  tcctaaactg  tctaggagga    60
tggacaagtt  catgctctat  cttctcactg  ctggcaagaa  agctttggct  gatggtggtg   120
taaccgaaca  agtcatggct  gagtttgaca  aagccaaatg  tggcattttg  attggctctg   180
cactgggtgg  catgaaggtc  tttcatgagg  ctattcaagc  tttgaagatc  tcttacaaga   240
agatgaatcc  tttttgtgtt  cctcttgcta  caactaacat  gggttctgct  atgctcgcta   300
ttgatctggt  ctggtctggt  ctaaatgtga  atgttatata  aacaaaatat  gaatgaacaa   360
ccactgacgt  ttcttttcaa  atgataaatt  aggggtggat  ggggccaaac  tactctatat   420
caagtgctac  aagcaacttt  tgcattctga  attcagctaa  ccacattatt  aagggtgaag   480
ctgtaagtat  ctcctaaact  ctgtttggta  gacttctctt  ctggttttac  tttattagac   540
tgtcttgtct  ttcccctaaa  cctttca                                         567
```

| SEQUENCES |
|---|

SEQ ID NO: 20 Artificial Sequence (from *Brassica napus*) meganuclease
recognition site of Kas2 mutant
```
gggtggatgg ggccaaacta ctctatatca  agtgctacaa gcaacttttg cattctgaat         60
tcagctaac                                                                  69
```

SEQ ID NO: 21 Artificial Sequence (from Brassica napus) amino acid
translation of meganuclease recognition site of Kas2 mutant
```
Gly Trp Met Gly Pro Asn Tyr Ser Ile Ser Ser Ala Thr Ser Asn Phe
1               5                   10                  15
Cys Ile Leu Asn Ser Ala Asn
            20
```

SEQ ID NO: 22 (*Brassica napus*) meganuclease recognition site of wild type
Kas2
```
ggtggatggg  gacaaactac tctatatcaa  gtgcttgtgc tacaagcaac ttttgcattc         60
tgaattcagc  taac                                                           74
```

SEQ ID NO: 23 (*Brassica napus*) amino acid translation of meganuclease
recognition site of wild type Kas2
```
Gly Trp Met Gly Thr Asn Tyr Ser Ile Ser Ser Ala Cys Ala Thr Ser
1               5                   10                  15
Asn Phe Cys Ile Leu Asn Ser Ala Asn
            20                  25
```

SEQ ID NO: 24 Artificial Sequence (from *Brassica napus*) partial sequence
for a Kas2 N12 mutant in a Cargill background (15 bp deletion in N12)
```
cgggtgagat  caaatctttc tcaactgaag  gatgggttgc tcctaaactg tctaggagga         60
tggacaagtt  catgctctat cttctcactg  ctggcaagaa agctttggct gatggtgtg        120
taaccgaaca  agtcatggct gagtttgaca  aagccaaatg tggcatttg attggctctg        180
cactgggtgg  catgaaggtc tttcatgagg  ctattcaagc tttgaagatc tcttacaaga       240
agatgaatcc  tttttgtgtt cctcttgcta  caactaacat gggttctgct atgctcgcta       300
ttgatctggt  ctggtctggt ctaaatgtaa  atgttatata aacaaaatat gaatgaacaa       360
ccactgacgt  ttcttttcaa atgataaatt  aggggtggat ggggccaaac tactctatat       420
caagcaactt  ttgcattctg aattcagcta  accacattat taagggtgaa gctgtaagta       480
tctcctaaac  tctgtttggt agacttctct  tctggtttta ctttattaga ctgtcttgtc       540
tttccctaa   accttca                                                       558
```

SEQ ID NO: 25 Artificial Sequence (from *Brassica napus*) meganuclease
recognition site of Kas2 mutant
```
ggggtggatg  gggccaaact actctatatc  aagcaacttt tgcattctga attcagctaa         60
c                                                                          61
```

SEQ ID NO: 26 Artificial Sequence (from *Brassica napus*) amino acid
translation of meganuclease recognition site of Kas2 mutant
```
Gly Trp Met Gly Pro Asn Tyr Ser Ile Ser Ser Asn Phe Cys Ile Leu
1               5                   10                  15
Asn Ser Ala Asn
            20
```

SEQ ID NO: 27 (*Brassica napus*) meganuclease recognition site of wild type
Kas2
```
ggggtggatg  gggacaaact actctatatc  aagtgcttgc gctacaagca acttttgcat         60
tctgaattca  gctaac                                                         76
```

SEQ ID NO: 28 (*Brassica napus*) amino acid translation of meganuclease
recognition site of wild type Kas2
```
Gly Trp Met Gly Thr Asn Tyr Ser Ile Ser Ser Ala Cys Ala Thr Ser
1               5                   10                  15
Asn Phe Cys Ile Leu Asn Ser Ala Asn
            20                  25
```

SEQ ID NO: 29 (*Brassica napus*) partial wild-type sequence for Kas2 in a
IMC201 background (N12)
```
cattttgatt  ggctctgcac tgggtggcat  gaaggtcttt catgaggcta ttcaagcttt         60
gaagatctct  tacaagaaga tgaatccttt  tgtgttcct cttgctacaa ctaacatggg        120
ttctgctatg  ctcgctattg atctggtctg  gtctgctcta aatgtgaatg ttatataaac       180
aaaatatgaa  tgaacaacca ctgacgtttc  ttttcaaatg ataaattagg ggtggatggg       240
gccaaactac  tctatatcaa gtgcttgtgc  tacaagcaac ttttgcattc tgaattcagc       300
taaccacatt  attaagggtg aagctgtaag  tatctcctaa actctgtttg gtagacttct       360
cttctggttc  tactttatta gactgtcttg  tctttcccct aaaccttca                   410
```

SEQ ID NO: 30 Artificial Sequence (from *Brassica napus*) partial sequence
for a Kas2 N12 mutant in a IMC201 background (13 bp deletion in N12)
```
cattttgatt  ggctctgcac tgggtggcat  gaaggtcttt catgaggcta ttcaagcttt         60
gaagatctct  tacaagaaga tgaatccttt  tgtgttcct cttgctacaa ctaacatggg        120
ttctgctatg  ctcgctattg atctggtctg  gtctggtcta aatgtgaatg ttatataaac       180
```

| SEQUENCES | | | | | |
|---|---|---|---|---|---|
| aaaatatgaa | tgaacaacca | ctgacgtttc | ttttcaaatg | ataaattagg | ggtggatggg | 240 |
| gccaaactac | tctatatcaa | gtgcaacttt | tgcattctga | attcagctaa | ccacattatt | 300 |
| aagggtgaag | ctgtaagtat | ctcctaaact | ctgtttggta | gacttctctt | ctggttctac | 360 |
| tttattagac | tgtcttgtct | ttcccctaaa | cctttca | | | 397 |

SEQ ID NO: 31 Artificial Sequence (from *Brassica napus*) meganuclease
recognition site of Kas2 mutant
gggtggatgg ggccaaacta ctctatatca agtgcaactt ttgcattctg aat    53

SEQ ID NO: 32 Artificial Sequence (from *Brassica napus*) amino acid
translation of meganuclease recognition site of Kas2 mutant
Gly Trp Met Gly Pro Asn Tyr Ser Ile Ser Ala Thr Phe Ala Phe
1               5                  10                 15

SEQ ID NO: 33 (*Brassica napus*) meganuclease recognition site of wild type
Kas2
gggtggatgg ggccaaacta ctctatatca agtgcttgtg ctacaagcaa cttttgcatt    60
ctgaat    66

SEQ ID NO: 34 (*Brassica napus*) amino acid translation of meganuclease
recognition site of wild type Kas2
Gly Trp Met Gly Pro Asn Tyr Ser Ile Ser Ser Ala Cys Ala Thr Ser
1               5                  10                 15
Asn Phe Cys Ile Leu Asn
            20

---

What is claimed is:

1. A method to mutate the genome of a *Brassica* plant cell at a target site comprising:
   a) inducing a double stranded DNA break at said target site, said double stranded break being induced by the introduction to said cell of at least one meganuclease which recognizes a recognition sequence at said target site in a Kas2 gene; and
   b) selecting a plant cell wherein said double stranded DNA break has been repaired resulting in a modification in the genome at said target site, wherein said modification is a substitution of at least one nucleotide, a deletion of at least one nucleotide, an insertion of at least one nucleotide or any combination thereof; wherein one Kas 2 allele on N2, one Kas2 allele on N12, or both Kas2 alleles on N2 and N12 are mutated.

2. The method of claim 1, wherein said plant cell is regenerated into a plant.

3. A method to produce a *Brassica* plant with reduced saturated fatty acids comprising:
   a) inducing a double stranded DNA break at a target site, said double stranded break being induced by the introduction to a plant cell of at least one meganuclease which recognizes a recognition sequence at said target site in a Kas2 gene; and
   b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof; and
   c) regenerating said plant cell(s) of b) into a plant;

wherein one Kas 2 allele on N2, one Kas2 allele on N12, or both Kas2 alleles on N2 and N12 are mutated; and wherein said mutation results in reduced production of saturated fatty acids by said plant as compared to a control plant of identical genetic background that has not been mutated by said at least one meganuclease and repair.

4. The method of claim 2, wherein said plant is crossed with another plant.

5. The method of claim 1, wherein the plant is *Brassica napus, Brassica juncea*, or *Brassica rapa*.

6. The method of claim 1, wherein the mutation is a deletion of one or more nucleotides.

7. The method of claim 6, further comprising at least one substitution mutation.

8. The method of claim 2, wherein the plant yields a reduction of stearic acid (18:0) of about 8% to about 17% as compared to a non-mutated plant of identical genetic background.

9. The method of claim 2, wherein the plant yields a reduction of palmitic acid (16:0) of about 2% to about 10% as compared to a non-mutated plant of identical genetic background.

10. The method of claim 2, wherein the plant yields an overall reduction in total saturated fatty acids of about 1% to about 7%.

* * * * *

SEQUENCE LISTING

<160> NUMBER OF SEQ IDS NOS: 40

<210> SEQ ID NO 1
<211> LENGTH: 2714
<212> TYPE: DNA
<213> ORGANISM: Brassica napus

<400> SEQUENCE: 1

| atggtggctg | cctcttcctg | ttacgcctat | ttggacttta | ggccttgcaa | tcactacaac | 60 |
| aacaacaaca | acgccttgtc | ttctctcttc | ggatcaaata | gtatttcttt | gaatcaaaac | 120 |
| cagagtagat | tgaaccgagc | aactaactcc | ggtagagcat | tcttcttttg | ccgcgtcttc | 180 |
| ctgttaaagt | ttttttttt | taatgtttgc | tcacacaagt | cttgtttca | tgttgttatg | 240 |
| gttttatgt | tattgggcaa | atgatgaaac | ttgtaggtaa | tttttattgt | gagttcaga | 300 |
| ctagatataa | ggactatgtg | gatacatagt | ttggagacct | gcataaatgg | cagtcaaact | 360 |
| atatataa | actatgaagt | tgcatggaac | ttaattgata | taatgccatt | gagatgaggt | 420 |
| ttatgaatag | tagctaatta | attttaagta | actccatcgt | caacttataa | tgtgttatgt | 480 |
| tgtttttagg | tagagccatg | gctattgcta | tgaatatgga | aaatgaagcc | atggttagca | 540 |
| agaataatcc | ccctatggag | aagcgtcggg | ttgtggtgac | aggcatggga | gttgaaacat | 600 |
| cattaggtca | tgacccacat | accttttacg | agaacttgct | acaaggaaac | agtggtatta | 660 |
| gccacattga | ggattttgat | tgttctgact | tcctacggt | aaataagcaa | atattattat | 720 |
| catattatat | caagactttc | ttggtatctt | tgtgggtttc | tttatttact | atctttcctt | 780 |
| tgtttttaaa | ttttgttcaa | gagaatcgcg | ggtgagatca | aatctttctc | cactgaagga | 840 |
| tgggttgctc | ctaaactgtc | taggaggatg | acaagttca | tgctctatct | cctcactgct | 900 |
| ggcaagaaag | ctttggctga | tggtggtgta | accgaacaag | tcatggctga | gtttgacaaa | 960 |
| gccaaatgtg | gcgttttgat | tggctctgca | ctgggtggca | tgaaggtctt | tcatgaggct | 1020 |
| attcaagctt | tgaagatctc | ttacaagaag | atgaatcctt | tttgtgttcc | tcttgctaca | 1080 |

```
actaacatgg gttctgctat gcttgctgtt gatctggtgt ctgattaaat ctgaatgtta      1140
atataaacaa atatgaatg aacaacactg acgtttcttt tcaaatgata aatagggggtg     1200 gatgggcca aactactcta tttcaagtgc ttgtgctaca agcaacttct gcattctgaa      1260
ttcagctaac cacattatta agggtgaagc tgtaagtatc ctacatccac ttggaaactc     1320
aaaagtttgg tagaactact ttattagact gtctcctaaa cctttcagga tgtaatgcta    1380
tgtggtggct cagatgcagc tattattcca ataggtgcaa actctctctc tctcctgcac    1440
tgctctttga agtttaagat acatgtatct tattgtatgt gtaccagtgc agggttggca    1500
ggtttcgtgg cagtccgggc tcttttcacaa aggaataatg atcccgcaaa agcttcacgt   1560
ccttgggatt gtgtaattt cttacactgc atcgaagttc tgtcaatagg accttccctt    1620
acatgtctgt aatgttgaag gaagtttaat gtgttgaaat gtgtgtatta tgtttttgta    1680
acagaatcga gatggtttcg tgattgggga gggagctgga gttctgcttt tggaagaact    1740
tgagcatgct aaggtatata acttattaca aatgaaactt atctcgttct tgccatggaa    1800
aaagttgtaa gaacttatgt attttgattt tatgttttca gaaaagagga gcaactatct    1860
acgcagagtt tcttggtggg agcttcacat gtgatgccta ccacatgacc gagcctcacc    1920
ctgatggtag tttcattttc ccctattcca tattagttg ccattaaccc atgtctaaat     1980
atccacagga gctggtgtga ttatatgtat tgagagagcg ttagctcatg ctgggattcc    2040
caaggaacag ataaattacg tcaatgcaca tgcaacctca acaccagctg gagaccttaa    2100
ggagtacaaa gccctggttc actgttttgg tcaaaatcct gaggtagttt cattttttca    2160
gtcctcaagt ttagtatctt agaaaatgtt acaagattcc aaggtagttt tatgtgcttt    2220
tcttatttgc tcctctcact atgttggcag ctaaaggtaa actccacgaa atcgatgatc    2280
ggacacttgc tgggagctgc tggtgctgta gaggctgttg caaccgtgca ggtaagacaa    2340
taaatattag agactgggtg cagttttctc agttttcatg ctaattttct tttggtttct    2400
aaaggcaata agaaccggtt gggttcatcc aaatatcaac ctagacaatc cagagaatgg   2460
agtggtatgt tgttgttttt tgccttattg ttattcaaag atgatcatat tttgatacta    2520
gtattctaca caaagaccat ttaatgtcca taataaaagt tttaataata ctacctaatg    2580
ttatgaaact ggagcaggat acaaaattgc tggtgggttc taagaaggag agattgaaca    2640
ttaaagcagc cttgtcaaat tcttttgggt ttggtggtca taactccagc atcattttg    2700 ctccttacaa gtga                                                      2714

<210> SEQ ID NO 2
<211> LENGTH: 455
<212> TYPE: DNA
<213> ORGANISM: Brassica napus

<400> SEQUENCE: 2
tgatggtggt gtaaccgaac aagtcatggc tgagtttgac aaagccaaat gtggcgtttt      60
gattggctct gcactgggtg gcatgaaggt cttttcatgag gctattcaag ctttgaagat    120
ctcttacaag aagatgaatc cttttttgtgt tcctcttgct acaactaaca tgggttctgc    180
tatgcttgct gttgatctgg tgtctgatta aatctgaatg ttaatataaa caaaatatga    240
atgaacaaca ctgacgtttc ttttcaaatg ataaataggg gtggatggg ccaaactact      300 ctatttcaag tgcttgtgct acaagcaact tctgcattct gaattcagct aaccacatta    360
ttaagggtga agctgtaagt atcctacatc cacttggaaa ctcaaaagtt tggtagaact    420
actttattag actgtctcct aaacctttca ggatg                                455
```

<210> SEQ ID NO 3
<211> LENGTH: 449
<212> TYPE: DNA
<213> ORGANISM: Artificial Sequence
<220> FEATURE:
<223> OTHER INFORMATION: from Brassica napus

<400> SEQUENCE: 3

```
tgatggtggt gtaaccgaac aagtcatggc tgagtttgac aaagccaaat gtggcgtttt      60
gattggctct gcactgggtg gcatgaaggt ctttcatgag ctattcaag ctttgaagat      120
ctcttacaag aagatgaatc ttttttgtgt tcctcttgct acaactaaca tgggttctgc     180
tatgcttgct gttgatctgg tgtctgatta aatctgaatg ttaatataaa caaatatga      240
atgaacaaca ctgacgtttc ttttcaaatg ataaataggg gtggatgggg ccaaactact     300
ctatttcaag tgctacaagc aacttctgca ttctgaattc agctaaccac attattaagg     360
gtgaagctgt aagtatccta catccacttg gaaactcaaa agtttggtag aactacttta     420
ttagactgtc tcctaaacct ttcaggatg                                       449
```

<210> SEQ ID NO 4
<211> LENGTH: 70
<212> TYPE: DNA
<213> ORGANISM: Artificial Sequence
<220> FEATURE:
<223> OTHER INFORMATION: from Brassica napus

<400> SEQUENCE: 4

```
ggggtggatg gggccaaact actctatttc aagtgctaca agcaacttct gcattctgaa      60
ttcagctaac                                                             70
```

<210> SEQ ID NO 5
<211> LENGTH: 23
<212> TYPE: PRT
<213> ORGANISM: Artificial Sequence
<220> FEATURE:
<223> OTHER INFORMATION: from Brassica napus

<400> SEQUENCE: 5

```
Gly Trp Met Gly Pro Asn Tyr Ser Ile Ser Ser Ala Thr Ser Asn Phe
1               5                   10                  15

Cys Ile Leu Asn Ser Ala Asn
            20
```

<210> SEQ ID NO 6
<211> LENGTH: 76
<212> TYPE: DNA
<213> ORGANISM: Brassica napus

<400> SEQUENCE: 6

```
ggggtggatg gggccaaact actctatttc aagtgcttgt gctacaagca acttctgcat      60
tctgaattca gctaac                                                      76
```

<210> SEQ ID NO 7
<211> LENGTH: 25
<212> TYPE: PRT
<213> ORGANISM: Brassica napus

<400> SEQUENCE: 7

```
Gly Trp Met Gly Pro Asn Tyr Ser Ile Ser Ser Ala Cys Ala Thr Ser
1               5                   10                  15
```

Asn Phe Cys Ile Leu Asn Ser Ala Asn
            20                  25

<210> SEQ ID NO 8
<211> LENGTH: 439
<212> TYPE: DNA
<213> ORGANISM: Artificial Sequence
<220> FEATURE:
<223> OTHER INFORMATION: from Brassica napus

<400> SEQUENCE: 8

| | | | | | |
|---|---|---|---|---|---|
| tgatggtggt | gtaaccgaac | aagtcatggc | tgagtttgac | aaagccaaat | gtggcgtttt | 60 |
| gattggctct | gcactgggtg | gcatgaaggt | ctttcatgag | gctattcaag | ctttgaagat | 120 |
| ctcttacaag | aagatgaatc | cttttgtgt | tcctcttgct | acaactaaca | tgggttctgc | 180 |
| tatgcttgct | gttgatctgg | tgtctgatta | aatctgaatg | ttaatataaa | caaaatatga | 240 |
| atgaacaaca | ctgacgtttc | ttttcaaatg | ataaataggg | gtggatgggg | ccaaactact | 300 |
| ctatttcaag | tgcttgtgca | ttctgaattc | agctaaccac | attattaagg | gtgaagctgt | 360 |
| aagtatccta | catccacttg | gaaactcaaa | agtttggtag | aactacttta | ttagactgtc | 420 |
| tcctaaacct | ttcaggatg | | | | | 439 |

<210> SEQ ID NO 9
<211> LENGTH: 63
<212> TYPE: DNA
<213> ORGANISM: Artificial Sequence
<220> FEATURE:
<223> OTHER INFORMATION: from Brassica napus

<400> SEQUENCE: 9

| | | | | | |
|---|---|---|---|---|---|
| ggggtggatg | gggccaaact | actctatttc | aagtgcttgt | gcattctgaa | ttcagctaac | 60 |
| cac | | | | | | 63 |

<210> SEQ ID NO 10
<211> LENGTH: 15
<212> TYPE: PRT
<213> ORGANISM: Artificial Sequence
<220> FEATURE:
<223> OTHER INFORMATION: from Brassica napus

<400> SEQUENCE: 10

Gly Trp Met Gly Pro Asn Tyr Ser Ile Ser Ser Ala Cys Ala Phe
1               5                   10                  15

<210> SEQ ID NO 11
<211> LENGTH: 79
<212> TYPE: DNA
<213> ORGANISM: Brassica napus

<400> SEQUENCE: 11

| | | | | | |
|---|---|---|---|---|---|
| ggggtggatg | gggccaaact | actctatttc | aagtgcttgt | gctacaagca | acttctgcat | 60 |
| tctgaattca | gctaaccac | | | | | 79 |

<210> SEQ ID NO 12
<211> LENGTH: 26
<212> TYPE: PRT
<213> ORGANISM: Brassica napus

<400> SEQUENCE: 12

Gly Trp Met Gly Pro Asn Tyr Ser Ile Ser Ser Ala Cys Ala Thr Ser
1               5                   10                  15

Asn Phe Cys Ile Leu Asn Ser Ala Asn His
          20                  25

<210> SEQ ID NO 13
<211> LENGTH: 573
<212> TYPE: DNA
<213> ORGANISM: Brassica napus

<400> SEQUENCE: 13
cgggtgagat caaatctttc tcaactgaag gatgggttgc tcctaaactg tctaggagga      60
tggacaagtt catgctctat cttctcactg ctggcaagaa gctttggct gatggtggtg     120 taaccgaaca agtcatggct gagtttgaca aagccaaatg tggcattttg attggctctg    180
cactgggtgg catgaaggtc tttcatgagg ctattcaagc tttgaagatc tcttacaaga    240
agatgaatcc tttttgtgtt cctcttgcta caactaacat gggttctgct atgctcgcta    300
ttgatctggt ctggtctggt ctaaatgtga atgttatata acaaaatat gaatgaacaa     360 ccactgacgt ttcttttcaa atgataaatt aggggtggat ggggccaaac tactctatat    420
caagtgcttg cgctacaagc aacttttgca ttctgaattc agctaaccac attattaagg    480
gtgaagctgt aagtatctcc taaactctgt ttggtagact tctcttctgg ttttacttta    540
ttagactgtc ttgtctttcc cctaaacctt tca                                 573

<210> SEQ ID NO 14
<211> LENGTH: 522
<212> TYPE: DNA
<213> ORGANISM: Artificial Sequence
<220> FEATURE:
<223> OTHER INFORMATION: from Brassica napus

<400> SEQUENCE: 14
cgggtgagat caaatctttc tcaactgaag gatgggttgc tcctaaactg tctaggagga      60
tggacaagtt catgctctat cttctcactg ctggcaagaa gctttggct gatggtggtg     120 taaccgaaca agtcatggct gagtttgaca aagccaaatg tggcattttg attggctctg    180
cactgggtgg catgaaggtc tttcatgagg ctattcaagc tttgaagatc tcttacaaga    240
agatgaatcc tttttgtgtt cctcttgcta caactaacat gggttctgct atgctcgcta    300
ttgatctggt ctggtctggt ctaaatgtga atgttatata acaaaatat gaatgaacaa     360 ccactgacgt ttcttttcaa atgataaatt aggggtggat ggggccaaac tactctatat    420
caagtgcttg tgaagctgta agtatctcct aaactctgtt tggtagactt ctcttctggt    480
tttactttat tagactgtct tgtctttccc ctaaacctt ca                        522

<210> SEQ ID NO 15
<211> LENGTH: 51
<212> TYPE: DNA
<213> ORGANISM: Artificial Sequence
<220> FEATURE:
<223> OTHER INFORMATION: from Brassica napus

<400> SEQUENCE: 15
tggatggggt ggatggggcc aaactactct atttcaagtg cttgtgaagc t              51

<210> SEQ ID NO 16
<211> LENGTH: 14
<212> TYPE: PRT
<213> ORGANISM: Artificial Sequence
<220> FEATURE:
<223> OTHER INFORMATION: from Brassica napus

<400> SEQUENCE: 16

Trp Met Gly Thr Asn Tyr Ser Ile Ser Ser Ala Cys Glu Ala
1               5                   10

<210> SEQ ID NO 17
<211> LENGTH: 102
<212> TYPE: DNA
<213> ORGANISM: Brassica napus

<400> SEQUENCE: 17
tggatggggt ggatggggcc aaactactct atttcaagtg cttgtgctac aagcaacttc    60
tgcattctga attcagctaa ccacattatt aagggtgaag ct                      102

<210> SEQ ID NO 18
<211> LENGTH: 31
<212> TYPE: PRT
<213> ORGANISM: Brassica napus

<400> SEQUENCE: 18

Trp Met Gly Thr Asn Tyr Ser Ile Ser Ser Ala Cys Ala Thr Ser Asn
1               5                   10                  15

Phe Cys Ile Leu Asn Ser Ala Asn His Ile Ile Lys Gly Glu Ala
            20                  25                  30

<210> SEQ ID NO 19
<211> LENGTH: 567
<212> TYPE: DNA
<213> ORGANISM: Artificial Sequence
<220> FEATURE:
<223> OTHER INFORMATION: from Brassica napus

<400> SEQUENCE: 19
cgggtgagat caaatctttc tcaactgaag gatgggttgc tcctaaactg tctaggagga    60
tggacaagtt catgctctat cttctcactg ctggcaagaa agctttggct gatggtggtg   120
taaccgaaca agtcatggct gagtttgaca agccaaatg tggcattttg attggctctg    180
cactgggtgg catgaaggtc tttcatgagg ctattcaagc tttgaagatc tcttacaaga   240
agatgaatcc ttttttgtgtt cctcttgcta caactaacat gggttctgct atgctcgcta   300
ttgatctggt ctggtctggt ctaaatgtga atgttatata acaaaatat gaatgaacaa    360 ccactgacgt ttcttttcaa atgataaatt aggggtggat ggggccaaac tactctatat    420
caagtgctac aagcaacttt tgcattctga attcagctaa ccacattatt aagggtgaag   480
ctgtaagtat ctcctaaact ctgtttggta gacttctctt ctggttttac tttattagac   540
tgtcttgtct ttcccctaaa cctttca                                       567

<210> SEQ ID NO 20
<211> LENGTH: 69
<212> TYPE: DNA
<213> ORGANISM: Artificial Sequence
<220> FEATURE:
<223> OTHER INFORMATION: from Brassica napus

<400> SEQUENCE: 20
gggtggatgg ggccaaacta ctctatatca agtgctacaa gcaacttttg cattctgaat    60
tcagctaac                                                           69

<210> SEQ ID NO 21
<211> LENGTH: 23

<212> TYPE: PRT
<213> ORGANISM: Artificial Sequence
<220> FEATURE:
<223> OTHER INFORMATION: from Brassica napus

<400> SEQUENCE: 21

Gly Trp Met Gly Pro Asn Tyr Ser Ile Ser Ser Ala Thr Ser Asn Phe
1               5                   10                  15

Cys Ile Leu Asn Ser Ala Asn
            20

<210> SEQ ID NO 22
<211> LENGTH: 74
<212> TYPE: DNA
<213> ORGANISM: Brassica napus

<400> SEQUENCE: 22
ggtggatggg gacaaactac tctatatcaa gtgcttgtgc tacaagcaac ttttgcattc    60
tgaattcagc taac                                                    74

<210> SEQ ID NO 23
<211> LENGTH: 25
<212> TYPE: PRT
<213> ORGANISM: Brassica napus

<400> SEQUENCE: 23

Gly Trp Met Gly Thr Asn Tyr Ser Ile Ser Ser Ala Cys Ala Thr Ser
1               5                   10                  15

Asn Phe Cys Ile Leu Asn Ser Ala Asn
            20                  25

<210> SEQ ID NO 24
<211> LENGTH: 558
<212> TYPE: DNA
<213> ORGANISM: Artificial Sequence
<220> FEATURE:
<223> OTHER INFORMATION: from Brassica napus

<400> SEQUENCE: 24
cgggtgagat caaatctttc tcaactgaag gatgggttgc tcctaaactg tctaggagga    60
tggacaagtt catgctctat cttctcactg ctggcaagaa agctttggct gatggtggtg   120
taaccgaaca agtcatggct gagtttgaca agccaaatg tggcattttg attggctctg   180
cactgggtgg catgaaggtc tttcatgagg ctattcaagc tttgaagatc tcttacaaga   240
agatgaatcc ttttgtgtt cctcttgcta caactaacat gggttctgct atgctcgcta   300
ttgatctggt ctggtctggt ctaaatgtga atgttatata aacaaaatat gaatgaacaa   360
ccactgacgt ttcttttcaa atgataaatt aggggtggag gggccaaac tactctatat   420 caagcaactt tgcattctg aattcagcta accacattat taagggtgaa gctgtaagta   480
tctcctaaac tctgtttggt agacttctct tctggtttta ctttattaga ctgtcttgtc   540 tttccccta acctttca                                                 558

<210> SEQ ID NO 25
<211> LENGTH: 61
<212> TYPE: DNA
<213> ORGANISM: Artificial Sequence
<220> FEATURE:
<223> OTHER INFORMATION: from Brassica napus

<400> SEQUENCE: 25

```
ggggtggatg gggccaaact actctatatc aagcaactt  tgcattctga attcagctaa      60
c                                                                     61
```

<210> SEQ ID NO 26
<211> LENGTH: 20
<212> TYPE: PRT
<213> ORGANISM: Artificial Sequence
<220> FEATURE:
<223> OTHER INFORMATION: from Brassica napus

<400> SEQUENCE: 26

```
Gly Trp Met Gly Pro Asn Tyr Ser Ile Ser Ser Asn Phe Cys Ile Leu
1               5                   10                  15

Asn Ser Ala Asn
            20
```

<210> SEQ ID NO 27
<211> LENGTH: 76
<212> TYPE: DNA
<213> ORGANISM: Brassica napus

<400> SEQUENCE: 27

```
ggggtggatg gggacaaact actctatatc aagtgcttgc gctacaagca acttttgcat      60
tctgaattca gctaac                                                     76
```

<210> SEQ ID NO 28
<211> LENGTH: 25
<212> TYPE: PRT
<213> ORGANISM: Brassica napus

<400> SEQUENCE: 28

```
Gly Trp Met Gly Thr Asn Tyr Ser Ile Ser Ser Ala Cys Ala Thr Ser
1               5                   10                  15

Asn Phe Cys Ile Leu Asn Ser Ala Asn
            20                  25
```

<210> SEQ ID NO 29
<211> LENGTH: 410
<212> TYPE: DNA
<213> ORGANISM: Brassica napus

<400> SEQUENCE: 29

```
cattttgatt ggctctgcac tgggtggcat gaaggtcttt catgaggcta ttcaagcttt      60
gaagatctct acaagaaga tgaatccttt tgtgttcct cttgctacaa ctaacatggg      120
ttctgctatg ctcgctattg atctggtctg gtctggtcta aatgtgaatg ttatataaac     180
aaaatatgaa tgaacaacca ctgacgtttc ttttcaaatg ataaattagg ggtggatggg     240
gccaaactac tctatatcaa gtgcttgtgc tacaagcaac ttttgcattc tgaattcagc     300
taaccacatt attaagggtg aagctgtaag tatctcctaa actctgtttg gtagacttct     360
cttctggttc tactttatta gactgtcttg tctttcccct aaacctttca                410
```

<210> SEQ ID NO 30
<211> LENGTH: 397
<212> TYPE: DNA
<213> ORGANISM: Artificial Sequence
<220> FEATURE:
<223> OTHER INFORMATION: from Brassica napus

<400> SEQUENCE: 30

```
cattttgatt ggctctgcac tgggtggcat gaaggtcttt catgaggcta ttcaagcttt      60
```

```
gaagatctct tacaagaaga tgaatccttt ttgtgttcct cttgctacaa ctaacatggg      120
ttctgctatg ctcgctattg atctggtctg gtctggtcta atgtgaatg ttatataaac       180 aaaatatgaa tgaacaacca ctgacgtttc ttttcaaatg ataaattagg ggtggatggg      240
gccaaactac tctatatcaa gtgcaacttt tgcattctga attcagctaa ccacattatt      300
aagggtgaag ctgtaagtat ctcctaaact ctgtttggta gacttctctt ctggttctac      360
tttattagac tgtcttgtct ttcccctaaa cctttca                              397
```

```
<210> SEQ ID NO 31
<211> LENGTH: 53
<212> TYPE: DNA
<213> ORGANISM: Artificial Sequence
<220> FEATURE:
<223> OTHER INFORMATION: from Brassica napus

<400> SEQUENCE: 31
gggtggatgg ggccaaacta ctctatatca agtgcaactt ttgcattctg aat            53
```

```
<210> SEQ ID NO 32
<211> LENGTH: 16
<212> TYPE: PRT
<213> ORGANISM: Artificial Sequence
<220> FEATURE:
<223> OTHER INFORMATION: from Brassica napus

<400> SEQUENCE: 32

Gly Trp Met Gly Pro Asn Tyr Ser Ile Ser Ser Ala Thr Phe Ala Phe
1               5                   10                  15
```

```
<210> SEQ ID NO 33
<211> LENGTH: 66
<212> TYPE: DNA
<213> ORGANISM: Brassica napus

<400> SEQUENCE: 33
gggtggatgg ggccaaacta ctctatatca agtgcttgtg ctacaagcaa cttttgcatt     60
ctgaat                                                                 66
```

```
<210> SEQ ID NO 34
<211> LENGTH: 22
<212> TYPE: PRT
<213> ORGANISM: Brassica napus

<400> SEQUENCE: 34

Gly Trp Met Gly Pro Asn Tyr Ser Ile Ser Ser Ala Cys Ala Thr Ser
1               5                   10                  15

Asn Phe Cys Ile Leu Asn
            20
```

```
<210> SEQ ID NO 35
<211> LENGTH: 62
<212> TYPE: DNA
<213> ORGANISM: Artificial Sequence
<220> FEATURE:
<223> OTHER INFORMATION: from Brassica napus

<400> SEQUENCE: 35
gggtggatgg ggccaaacta ctctatttca agtgcttgtg cattctgaat tcagctaacc     60
ac                                                                     62
```

```
<210> SEQ ID NO 36
<211> LENGTH: 78
<212> TYPE: DNA
<213> ORGANISM: Brassica napus

<400> SEQUENCE: 36
gggtggatgg ggccaaacta ctctatttca agtgcttgtg ctacaagcaa cttctgcatt      60
ctgaattcag ctaaccac                                                   78

<210> SEQ ID NO 37
<211> LENGTH: 42
<212> TYPE: DNA
<213> ORGANISM: Artificial Sequence
<220> FEATURE:
<223> OTHER INFORMATION: from Brassica napus

<400> SEQUENCE: 37
tggatggggc caaactactc tatatcaagt gcttgtgaag ct                        42

<210> SEQ ID NO 38
<211> LENGTH: 14
<212> TYPE: PRT
<213> ORGANISM: Artificial Sequence
<220> FEATURE:
<223> OTHER INFORMATION: from Brassica napus

<400> SEQUENCE: 38

Trp Met Gly Pro Asn Tyr Ser Ile Ser Ser Ala Cys Glu Ala
1               5                   10

<210> SEQ ID NO 39
<211> LENGTH: 93
<212> TYPE: DNA
<213> ORGANISM: Brassica napus

<400> SEQUENCE: 39
tggatgggga caaactactc tatatcaagt gcttgcgcta caagcaactt ttgcattctg      60
aattcagcta accacattat taagggtgaa gct                                  93

<210> SEQ ID NO 40
<211> LENGTH: 75
<212> TYPE: DNA
<213> ORGANISM: Brassica napus

<400> SEQUENCE: 40
gggtggatgg ggacaaacta ctctatatca agtgcttgcg ctacaagcaa cttttgcatt      60
ctgaattcag ctaac                                                      75
```